United States Patent
Hull et al.

(10) Patent No.: US 9,439,728 B2
(45) Date of Patent: Sep. 13, 2016

(54) SYSTEMS FOR CREATING ARTERIOVENOUS (AV) FISTULAS

(71) Applicants: Jeffrey E. Hull, Midlothian, VA (US); Mark A. Ritchart, Dana Point, CA (US); David K Wrolstad, Yucaipa, CA (US)

(72) Inventors: Jeffrey E. Hull, Midlothian, VA (US); Mark A. Ritchart, Dana Point, CA (US); David K Wrolstad, Yucaipa, CA (US)

(73) Assignees: Avenu Medical, Inc., San Juan Capistrano, CA (US); Baja Research, LLC, San Clemente, CA (US)

( * ) Notice: Subject to any disclaimer, the term of this patent is extended or adjusted under 35 U.S.C. 154(b) by 0 days.

(21) Appl. No.: 14/096,973

(22) Filed: Dec. 4, 2013

(65) Prior Publication Data
US 2014/0094791 A1    Apr. 3, 2014

Related U.S. Application Data

(63) Continuation of application No. 13/161,182, filed on Jun. 15, 2011.

(60) Provisional application No. 61/354,903, filed on Jun. 15, 2010, provisional application No. 61/480,486, filed on Apr. 29, 2011.

(51) Int. Cl.
*A61B 18/08* (2006.01)
*A61B 18/14* (2006.01)
(Continued)

(52) U.S. Cl.
CPC ............ *A61B 18/18* (2013.01); *A61B 17/11* (2013.01); *A61B 18/082* (2013.01);
(Continued)

(58) Field of Classification Search
CPC .......... A61B 2018/00404; A61B 2018/00416; A61B 2018/00422; A61B 2018/00488; A61B 2018/00482; A61B 2018/005; A61B 2018/00386; A61B 17/11; A61B 17/1114; A61B 17/1128; A61B 17/1146; A61B 2017/1107; A61B 2017/1121; A61B 2017/1135; A61B 2017/1139; A61B 2018/1475; A61B 17/32053; A61B 2017/00243
USPC .............................. 606/48–52, 184
See application file for complete search history.

(56) References Cited

U.S. PATENT DOCUMENTS 4,311,143 A  *  1/1982  Komiya ......................... 606/47
5,290,278 A     3/1994  Anderson
(Continued)

FOREIGN PATENT DOCUMENTS

| DE | 202010013152 | * | 4/2011 | ............. A61B 18/14 |
| JP | 2006280662 A | * | 10/2006 | |
| JP | 2008049157 | | 3/2008 | |

OTHER PUBLICATIONS

International Searching Authority, International Search Report and Written Opinion, corresponding to PCT/US2011/040530, filed Jun. 15, 2011.

(Continued)

*Primary Examiner* — Jaymi Della
(74) *Attorney, Agent, or Firm* — Donald E. Stout; Stout, Uxa & Buyan, LLP

(57) ABSTRACT

A system for creating an arteriovenous (AV) fistula comprises a vessel access sheath having a hollow interior and an exit port, a side access needle catheter configured to fit within the hollow interior of the sheath, a needle configured to be inserted into a blood vessel through the side access needle catheter, a toggle delivery catheter configured to fit within the hollow interior of the sheath, and a toggle apparatus configured to be delivered into a vessel through the toggle delivery catheter. The toggle apparatus comprises a shaft and a toggle member pivotably attached to a distal end of the shaft. A source of RF energy or resistive heat energy may be provided for application to the toggle member and/or to a heater insert in the toggle delivery catheter, for the purpose of creating the fistula.

17 Claims, 21 Drawing Sheets

(51) Int. Cl.
  *A61B 18/18* (2006.01)
  *A61B 17/11* (2006.01)
  *A61B 18/00* (2006.01)

(52) U.S. Cl.
  CPC ... *A61B 18/1492* (2013.01); *A61B 2017/1107* (2013.01); *A61B 2017/1139* (2013.01); *A61B 2018/00386* (2013.01); *A61B 2018/00601* (2013.01); *A61B 2018/00619* (2013.01); *A61B 2018/00714* (2013.01); *A61B 2018/1425* (2013.01); *A61B 2018/1475* (2013.01)

(56) References Cited

U.S. PATENT DOCUMENTS

| | | |
|---|---|---|
| 5,425,731 A | 6/1995 | Daniel et al. |
| 5,531,677 A | 7/1996 | Lundquist et al. |
| 5,769,086 A | 6/1998 | Ritchart et al. |
| 5,830,222 A | 11/1998 | Makower |
| 5,830,224 A | 11/1998 | Cohn et al. |
| 5,893,369 A * | 4/1999 | LeMole ............ 606/184 |
| 6,068,637 A | 5/2000 | Popov et al. |
| 6,068,638 A | 5/2000 | Makower |
| 6,071,292 A | 6/2000 | Makower et al. |
| 6,083,223 A | 7/2000 | Baker |
| 6,099,542 A | 8/2000 | Cohn et al. |
| 6,190,353 B1 | 2/2001 | Makower et al. |
| 6,235,027 B1 | 5/2001 | Herzon |
| 6,248,117 B1 | 6/2001 | Blatter |
| 6,283,983 B1 | 9/2001 | Makower et al. |
| 6,302,875 B1 | 10/2001 | Makower et al. |
| 6,330,884 B1 | 12/2001 | Kim |
| 6,352,535 B1 | 3/2002 | Lewis et al. |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,464,665 B1 | 10/2002 | Heuser |
| 6,524,308 B1 | 2/2003 | Muller et al. |
| 6,533,778 B2 | 3/2003 | Herzon |
| 6,544,230 B1 | 4/2003 | Flaherty et al. |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,669,709 B1 | 12/2003 | Cohn et al. |
| 6,699,245 B2 | 3/2004 | Dinger et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,159,592 B1 | 1/2007 | Makower et al. |
| 7,191,015 B2 | 3/2007 | Lamson et al. |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 2001/0034518 A1 * | 10/2001 | Edwards et al. ............ 606/41 |
| 2002/0188294 A1 | 12/2002 | Couture et al. |
| 2003/0114850 A1 * | 6/2003 | McClurken ...... A61B 18/1442 606/50 |
| 2004/0073238 A1 * | 4/2004 | Makower ................ 606/153 |
| 2004/0082945 A1 * | 4/2004 | Clague et al. ............ 606/32 |
| 2004/0167514 A1 * | 8/2004 | Okada ..................... 606/45 |
| 2004/0210215 A1 * | 10/2004 | Okada ..................... 606/45 |
| 2005/0021016 A1 * | 1/2005 | Malecki ........ A61B 17/0057 606/27 |
| 2005/0033330 A1 | 2/2005 | Vargas et al. |
| 2005/0038457 A1 | 2/2005 | Vargas et al. |
| 2005/0216042 A1 | 9/2005 | Gertner |
| 2006/0009759 A1 | 1/2006 | Chrisitian et al. |
| 2006/0030849 A1 | 2/2006 | Mirizzi et al. |
| 2006/0079873 A1 * | 4/2006 | Scopton ..... A61B 17/320016 606/37 |
| 2006/0111704 A1 | 5/2006 | Brenneman et al. |
| 2006/0142788 A1 | 6/2006 | Wilson et al. |
| 2006/0189979 A1 | 8/2006 | Esch et al. |
| 2006/0217697 A1 | 9/2006 | Lau et al. |
| 2006/0217706 A1 | 9/2006 | Lau et al. |
| 2006/0276784 A1 * | 12/2006 | Miyajima ....... A61B 18/1492 606/46 |
| 2006/0293738 A1 * | 12/2006 | Cross et al. ............ 607/122 |
| 2007/0123852 A1 * | 5/2007 | Deem et al. ............ 606/45 |
| 2008/0033425 A1 * | 2/2008 | Davis .......... A61B 17/0057 606/41 |
| 2009/0105662 A1 * | 4/2009 | Levedusky et al. ........ 604/192 |
| 2009/0270882 A1 | 10/2009 | O'Neill |
| 2010/0023132 A1 | 1/2010 | Imran |
| 2010/0145331 A1 | 6/2010 | Chrisitian et al. |
| 2010/0152723 A1 | 6/2010 | Esch et al. |
| 2011/0095067 A1 | 4/2011 | Ohdaira |
| 2011/0152861 A1 * | 6/2011 | Weisshaupt ........ A61B 17/11 606/48 |
| 2011/0251608 A1 | 10/2011 | Timm et al. |
| 2011/0251609 A1 | 10/2011 | Johnson et al. |
| 2011/0288546 A1 | 11/2011 | Abbott et al. |
| 2012/0078246 A1 | 3/2012 | Mirizzi et al. |
| 2012/0302935 A1 | 11/2012 | Miller et al. |
| 2012/0316550 A1 | 12/2012 | Lau et al. |

OTHER PUBLICATIONS

Office Action for U.S. Appl. No. 13/763,501, mailed on Feb. 29, 2016.

* cited by examiner

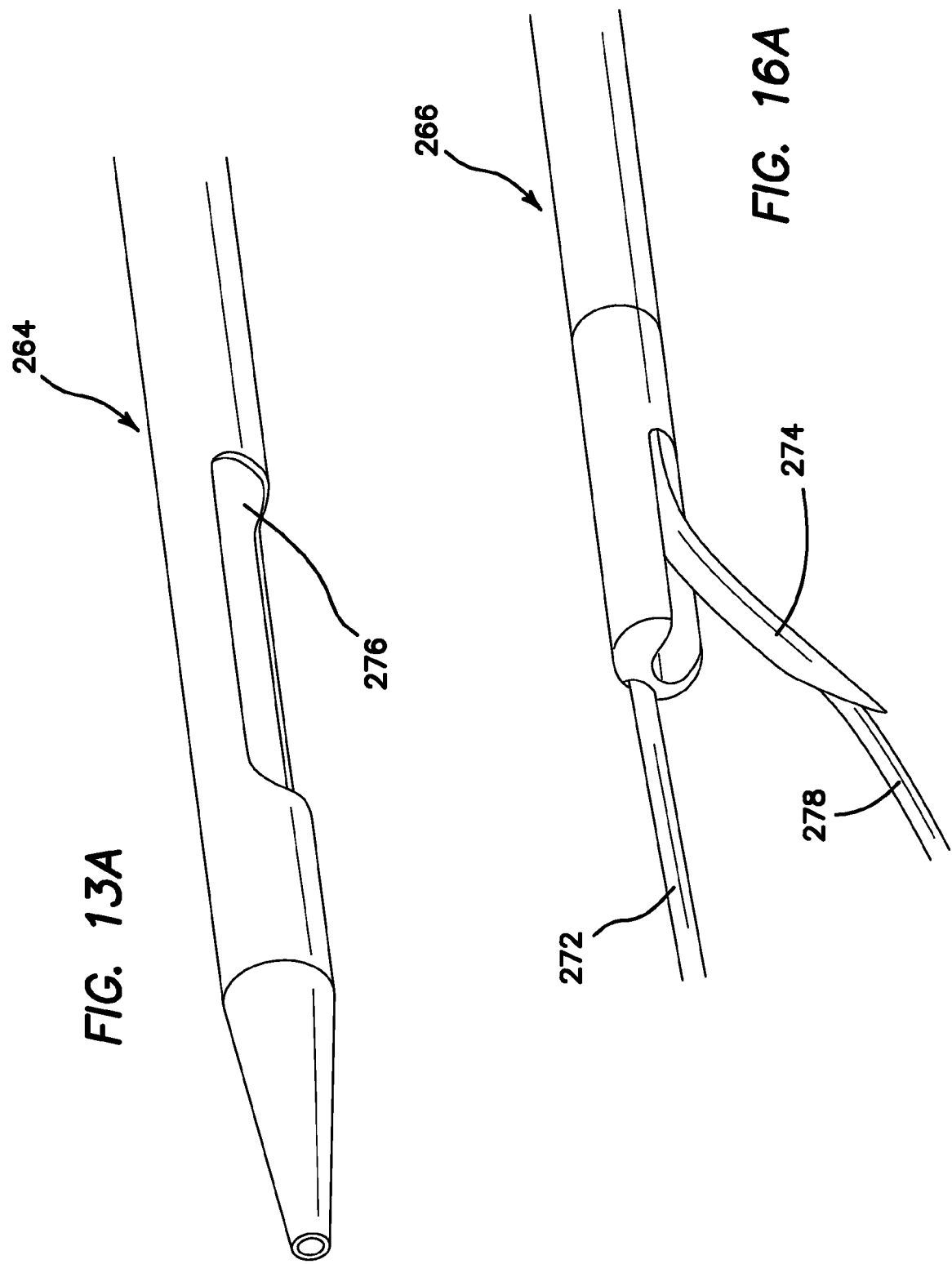

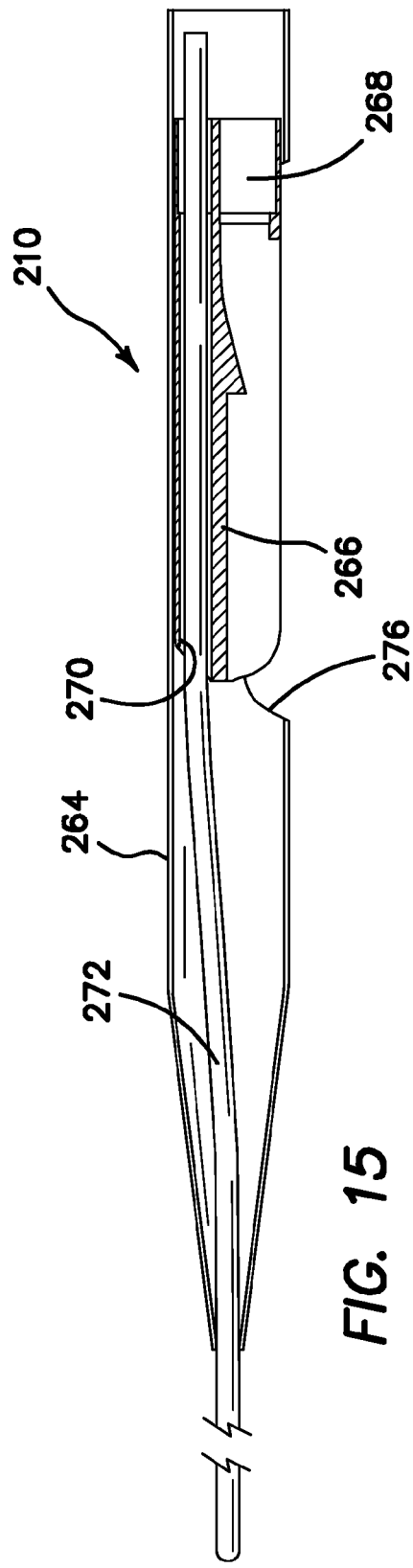
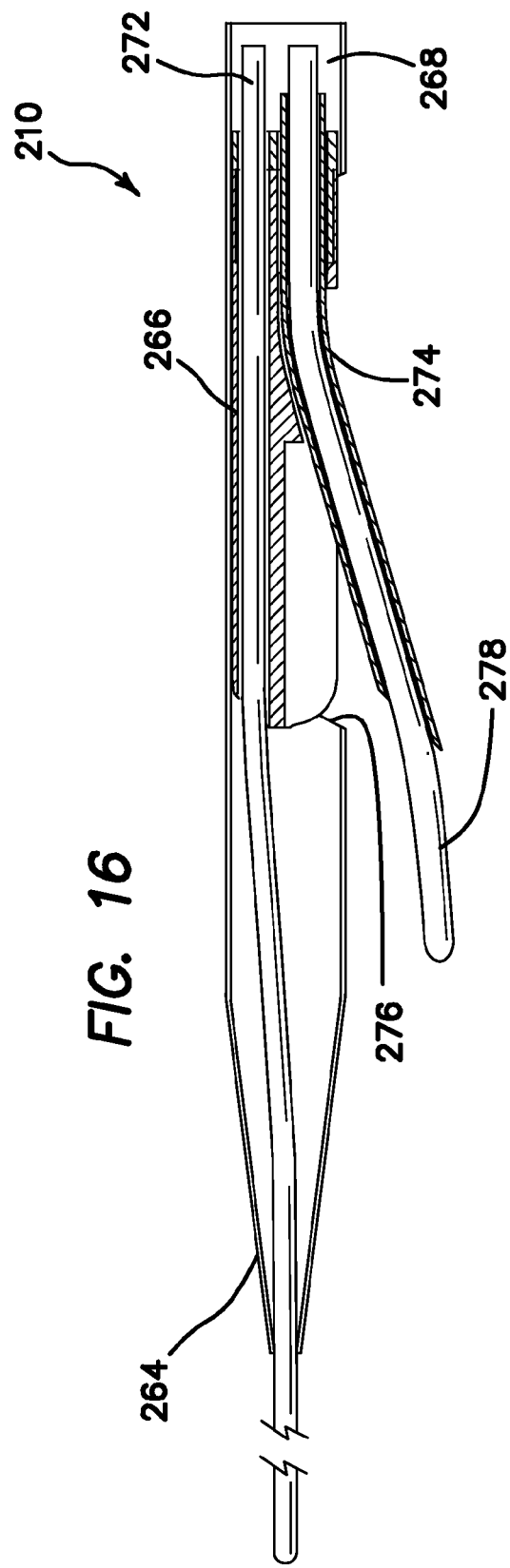
FIG. 15
FIG. 16

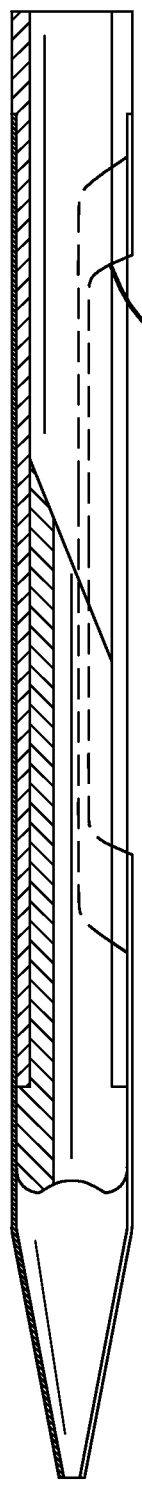
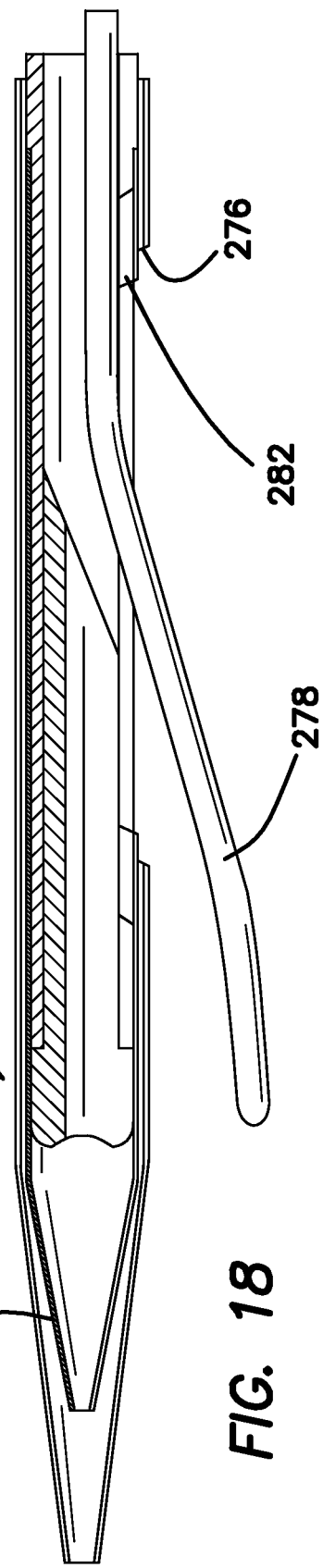

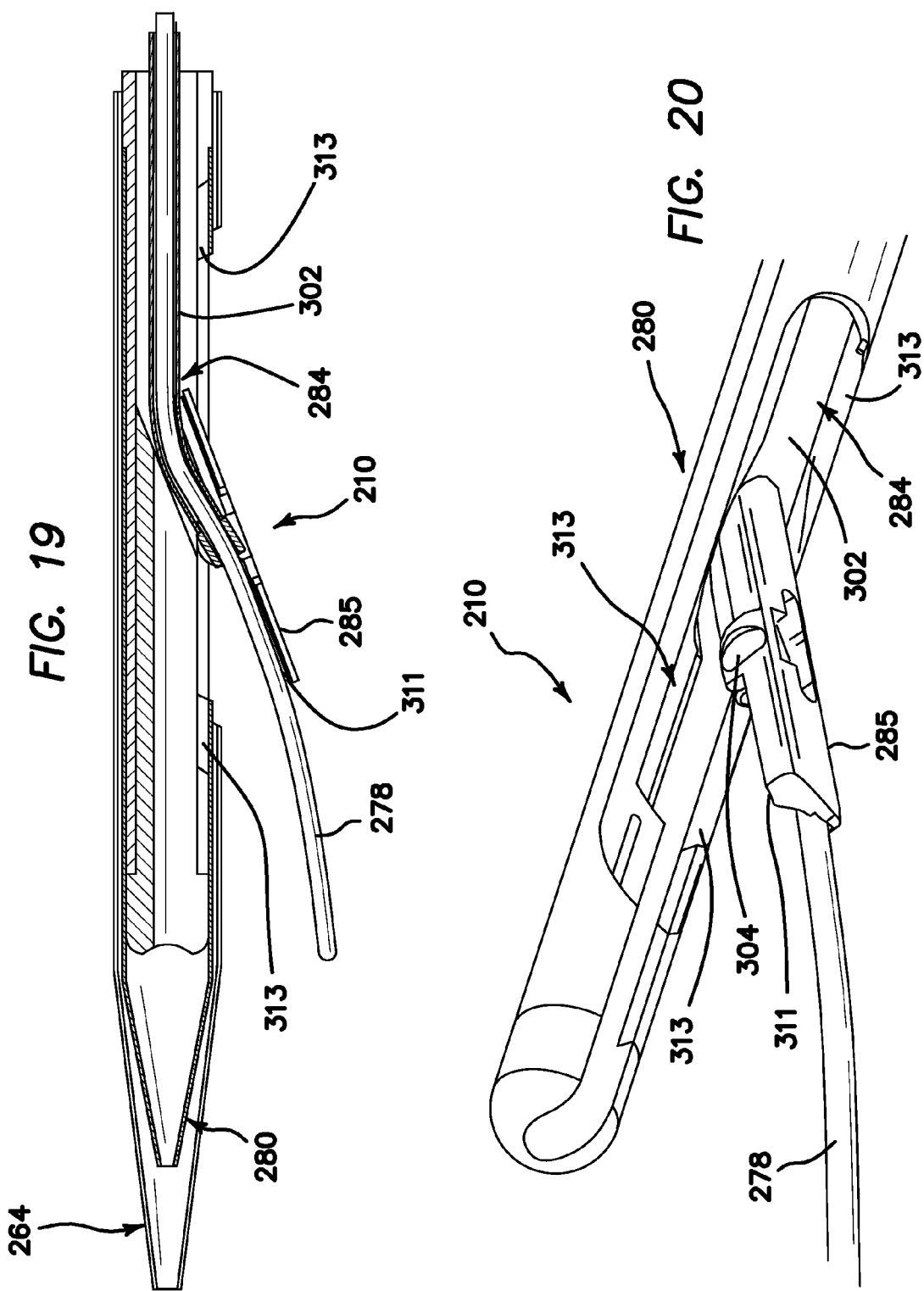

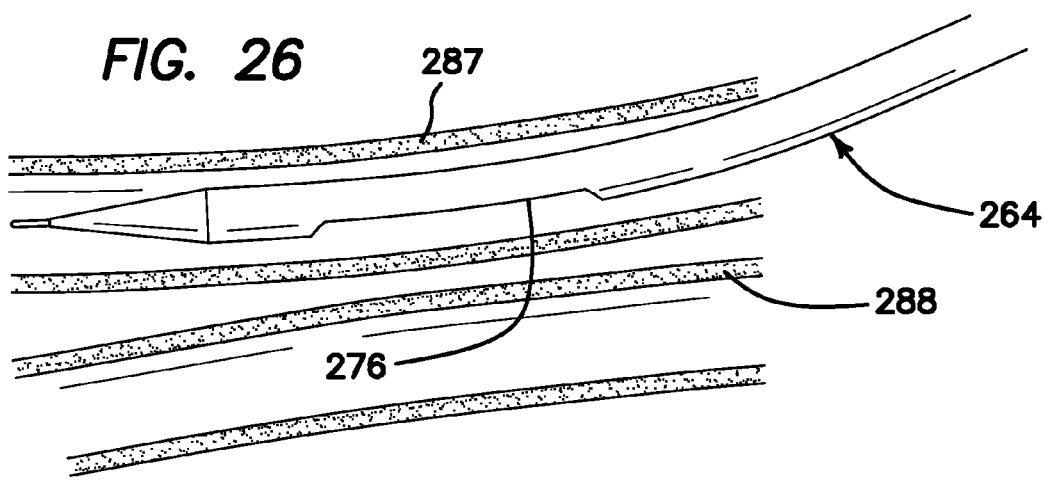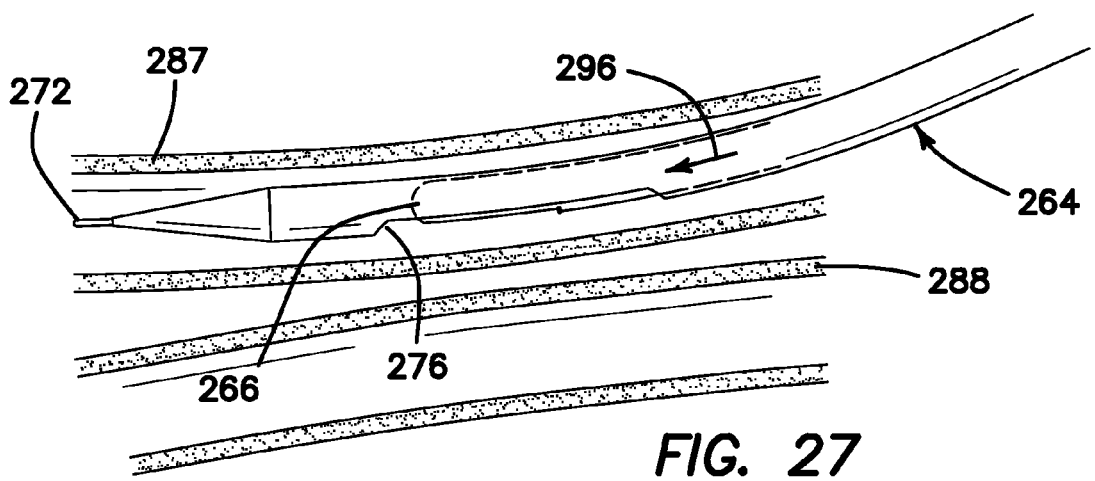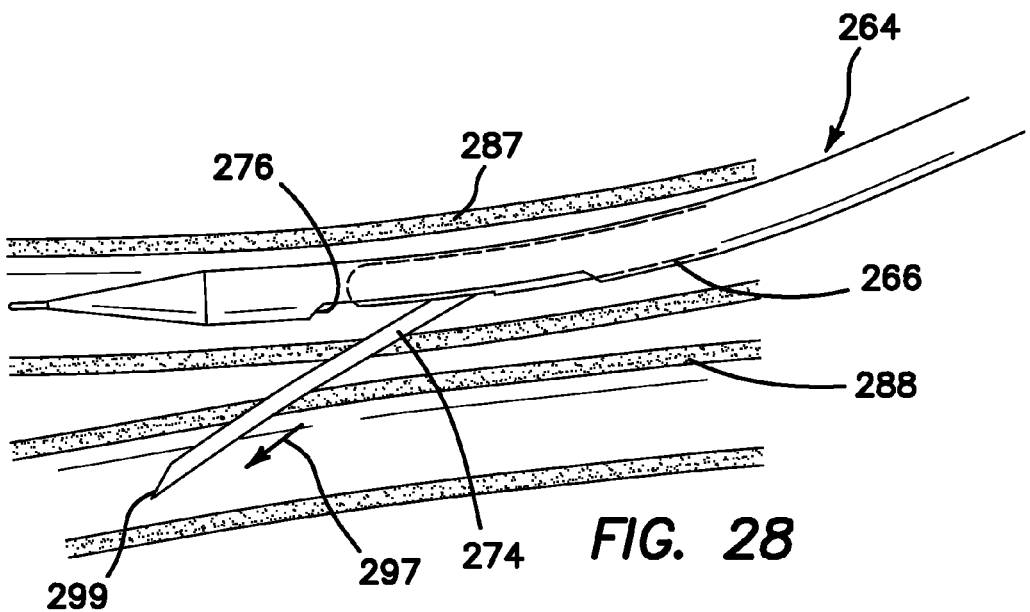

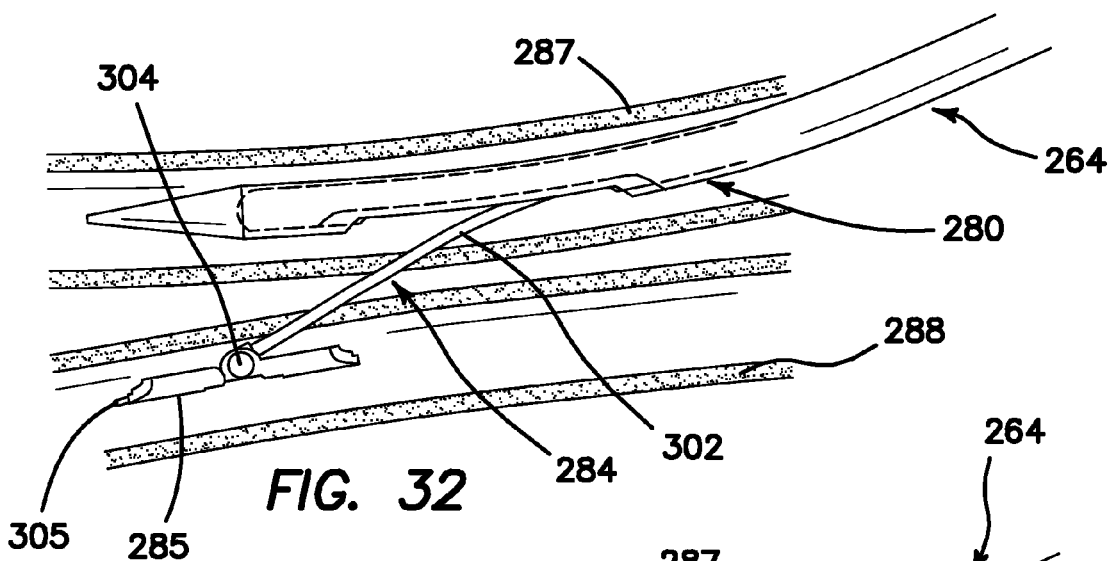
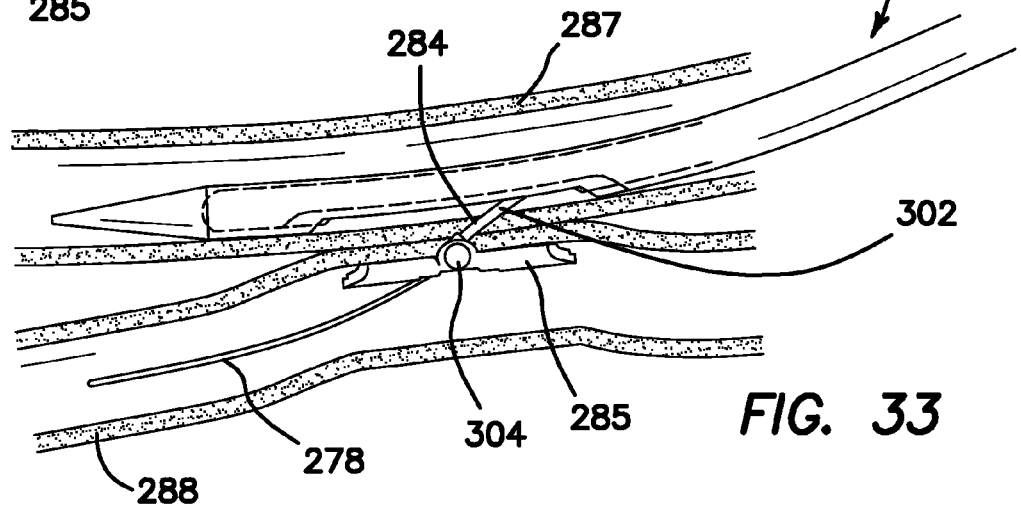
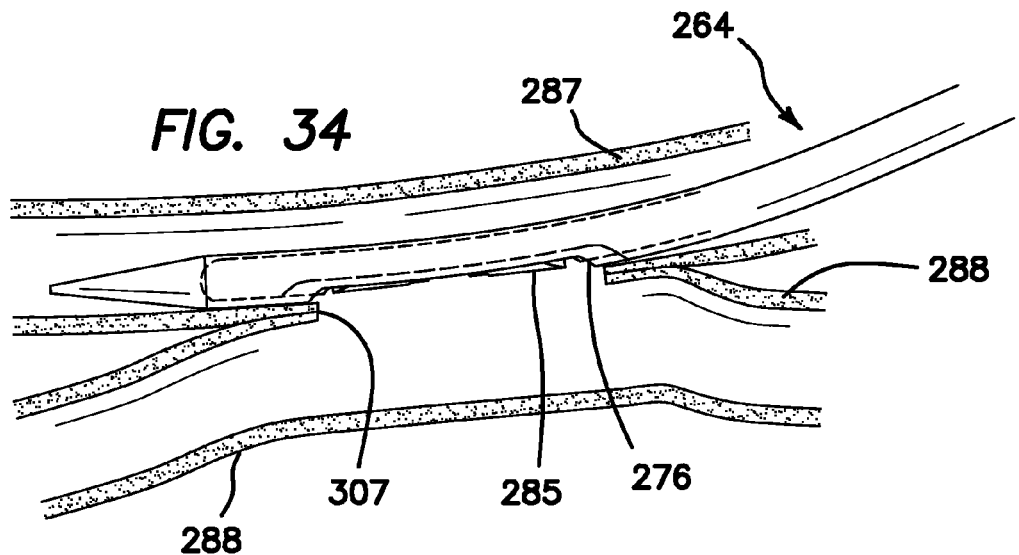

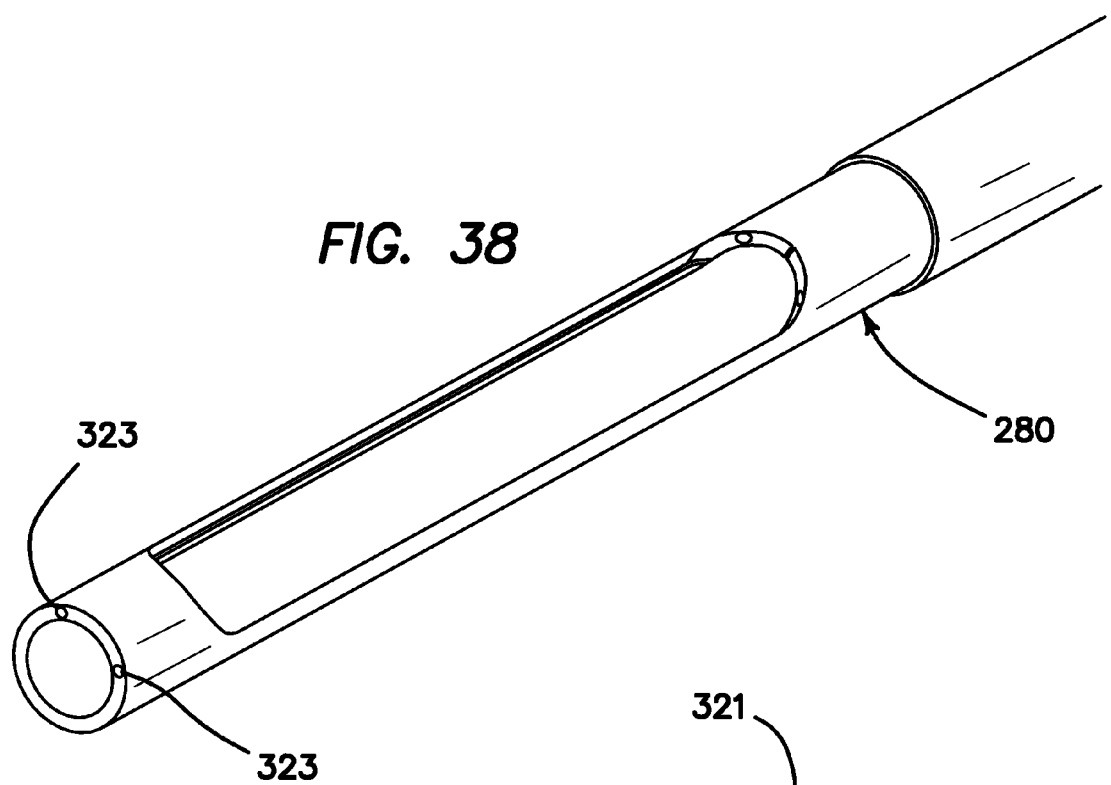
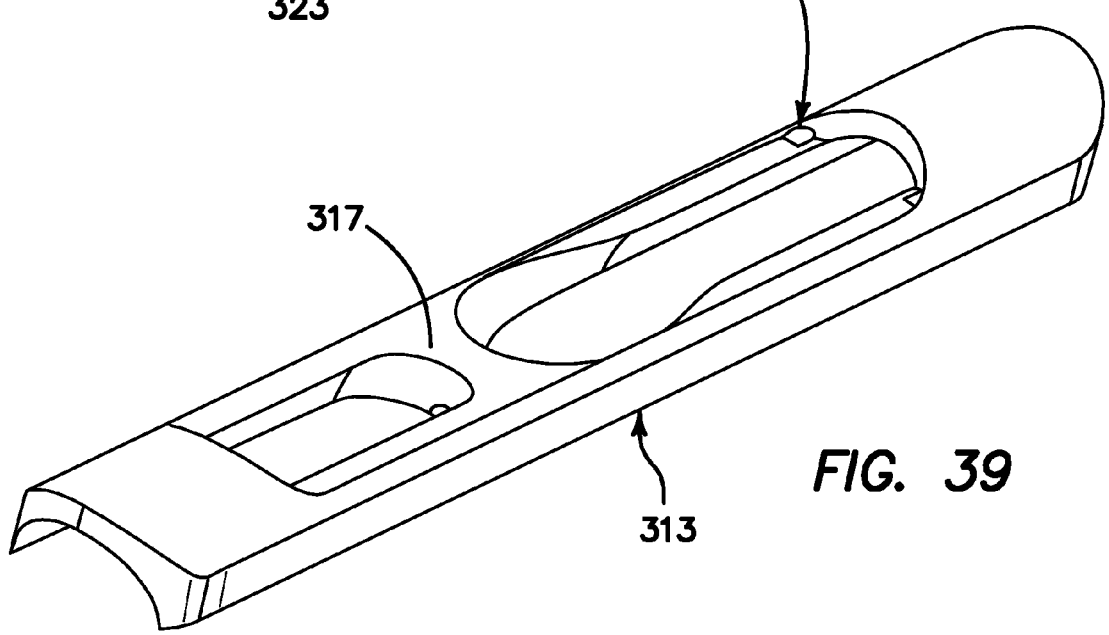

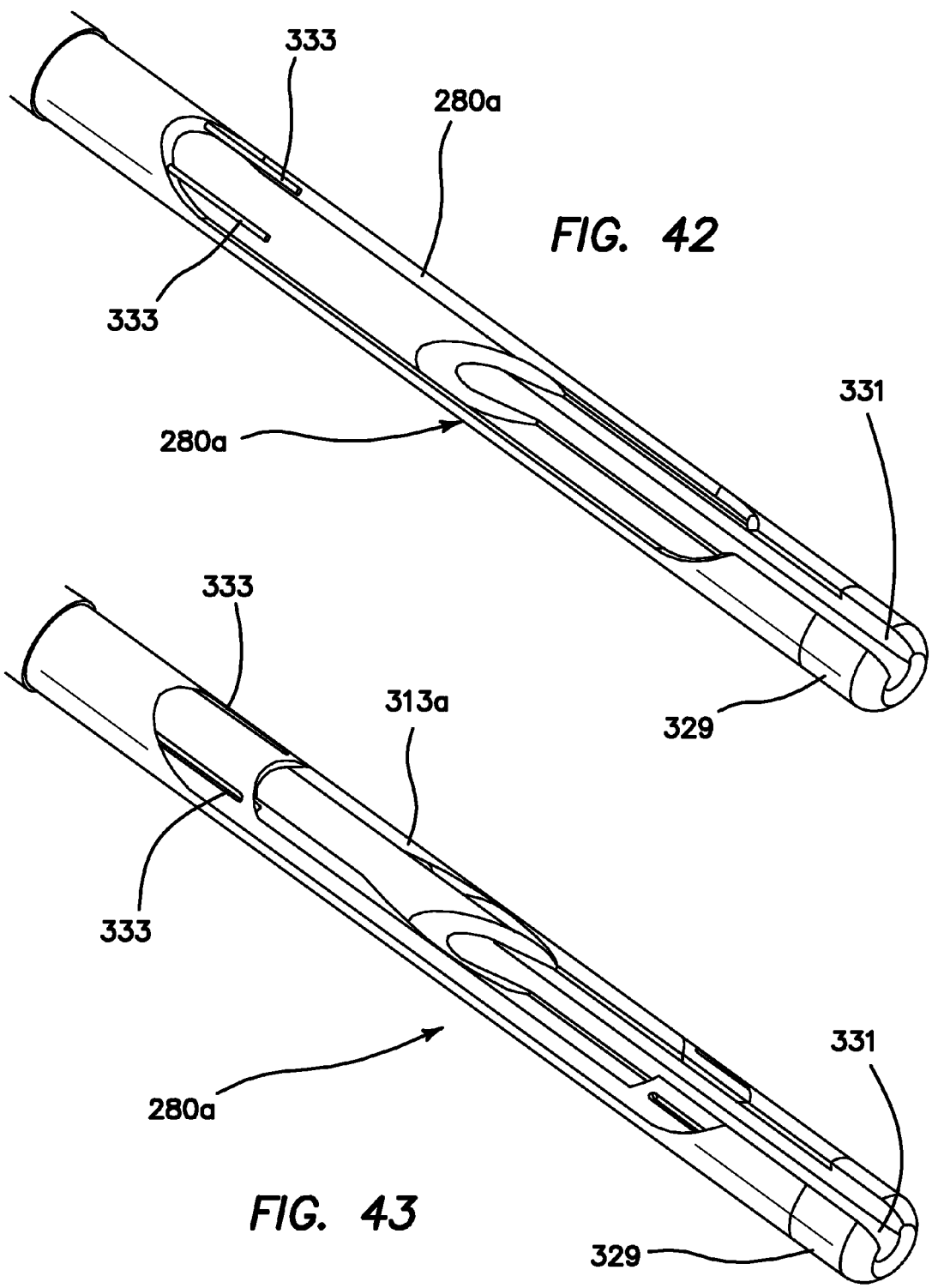

SYSTEMS FOR CREATING ARTERIOVENOUS (AV) FISTULAS

This application is a continuation application under 35 U.S.C. 120 of commonly assigned U.S. patent application Ser. No. 13/161,182, entitled Systems and Methods for Creating Arteriovenous (AV) Fistulas, filed Jun. 15, 2011, which in turn claims the benefit under 35 U.S.C. 119(e) of the filing date of Provisional U.S. Application Ser. No. 61/354,903, entitled Systems and Methods for Creating Arteriovenous Fistulas, filed on Jun. 15, 2010, and Provisional U.S. Application Ser. No. 61/480,486, entitled Systems and Methods for Creating Arteriovenous Fistulas, filed on Apr. 29, 2011. Each of the above referenced applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with catheters placed in large veins, prosthetic grafts attached to an artery and a vein, or a fistula where an artery is attached directly to the vein.

Fistulas for hemodialysis are required by patients with kidney failure. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater. Dialysis fistulas have to be close to the skin (<6 mm), and large enough (>4 mm) to access with a large needle. The fistula needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention comprises, in one aspect thereof, a device for creating an arteriovenous (AV) fistula, which comprises a first member or main body having a primary lumen and a secondary lumen, and a second or piercing member disposed in the secondary lumen, and configured to be moved distally out of the secondary lumen, and to cut through tissue while being distally moved. A third member extends from a distal end of the piercing member and is actuatable to move adjacent first and second blood vessels toward one another, and to create an elongated communicating aperture in opposing sides of each of the first vessel and the second vessel. In one particular embodiment, the third member comprises a toggle member which is hinged to a distal end of the piercing member, and is pivotable between first and second orientations relative to the piercing member. The toggle member may have a sharp point on one end thereof.

A source of RF energy or resistive heat energy may be provided for application to the toggle member, for the purpose of creating the elongated communicating aperture. Other cutting mechanisms known to those skilled in the art may alternatively be provided.

The third member comprises a pre-formed needle which is extendable from a distal end of the piercing member into a distal end of the primary lumen of the main body. A snare or other suitable apparatus is disposed in the primary lumen for retracting in a proximal direction the needle.

In another aspect of the invention, a method of creating an AV fistula between adjacent first and second blood vessels comprises a step of positioning a main body of a device within the first vessel and extending a piercing member distally from the main body, through a wall of the first vessel, and through an adjacent wall of the second vessel, so that a distal end of the piercing member is disposed within the second vessel. A third member is actuated to move relative to a distal end of the piercing member for cutting an elongated communicating aperture on opposing walls of the first vessel and the second vessel. Preferably, the positioning step is performed percutaneously. The third member preferably comprises a pivotable toggle member, and the actuating step comprises pivoting the toggle member relative to the distal end of the piercing member. The actuating step further comprises applying a proximally directed tensile force on the toggle member so that the toggle member pulls the second vessel toward the first vessel.

In one alternative, the inventive method further comprises a step of energizing the toggle member with RF energy, to cause a cutting action along the opposing walls of the first vessel and second vessel, in order to create the elongated communicating aperture. In another alternative, this further step is performed by energizing the toggle member with resistive heat energy, for the same purpose. In certain embodiments, the third member may comprise a pre-formed piercing needle and the actuating step comprises moving the pre-formed piercing needle so that an end thereof enters a distal end of the primary lumen. In these embodiments, the device further comprises a snare on a pull wire, disposed in the primary lumen, and the actuating step further comprises using the snare to capture the pre-formed piercing needle.

The method further comprises a step of pulling the pull wire proximally, thereby moving the preformed piercing needle proximally to cause a cutting action along the opposing walls of the first vessel and second vessel, in order to create the elongated communicating aperture.

In another aspect of the invention, there is provided a system for creating an arteriovenous (AV) fistula, which comprises a vessel access sheath having a hollow interior and an exit port, a side access needle catheter configured to fit within the hollow interior of the sheath, a needle configured to be inserted into a blood vessel through the side access needle catheter, a toggle delivery catheter configured to fit within the hollow interior of the sheath, and a toggle apparatus configured to be delivered into a vessel through the toggle delivery catheter. The toggle apparatus comprises a shaft and a toggle member pivotably attached to a distal end of the shaft.

A source of RF energy or resistive heat energy may be provided for application to the toggle member, for purposes that may include creating an elongated communicating aperture between two adjacent blood vessels, such as an artery and a vein, or applying energy to the vessel surface that opposes the toggle member. Other cutting mechanisms known to those skilled in the art may alternatively be provided.

The side access needle catheter preferably comprises a primary lumen and a secondary lumen. The toggle member may be actuated between an extended distal position and a retracted proximal position using the shaft.

A heater may be provided in the toggle delivery catheter for the purpose of creating an elongated communicating aperture between two adjacent vessels. In such a case, the heater may comprise a heater insert which is structurally separate from, or, alternatively, integral with the toggle delivery catheter. In the structurally separate embodiments, the heater insert may be removed from the toggle delivery catheter. Preferably, the heater insert comprises a surface which is adapted to mate with the toggle member when the toggle member is retracted to a proximal position, and comprises a resistive material. The heater insert may also comprise a weld cut zone and a guide wire slot, as well as apertures for conveying power wires to the heater insert.

In a presently preferred embodiment, the aforementioned source of RF or resistive heat energy is applied both to the toggle member and to the heater insert, for the purpose of creating an elongated communicating aperture between two adjacent vessels.

In yet another aspect of the invention, there is disclosed a method of creating an AV fistula between adjacent first and second vessels, comprising steps of inserting a first guidewire into the first vessel, positioning a hollow vessel access sheath within the first vessel over the first guidewire, inserting a needle into the sheath, and using the needle to pierce a side wall of the first vessel and a side wall of the adjacent second vessel. Additional method steps include advancing the needle so that a distal end thereof enters the second vessel, inserting a second guidewire through the needle from the first vessel into the second vessel, withdrawing the first guidewire and the needle from the procedural site, and inserting a toggle delivery catheter into the sheath over the second guidewire. At this juncture, a toggle apparatus comprising a shaft and a pivotable toggle member attached to a distal end of the shaft is advanced over the second guidewire so that the toggle member is disposed within the second vessel. The toggle member is moved proximally to contact the wall of the second vessel, and an aperture is created through the wall of one of the two vessels. Alternative approaches may include removing tissue roughly the size and shape of the toggle member via burning or vaporization. The toggle member moving step includes pivoting the toggle member so that the length of the toggle member is in contact with the wall of the second vessel.

In one approach according to the inventive method, the aperture creating step comprises a step of creating the aperture through the walls of both vessels, wherein the apertures in the walls of each of the first and second vessels together create a communicating aperture between said vessels to create said AV fistula. Advantageously, as the energized member (or members) cuts or ablates the tissue to create the communicating aperture, the tissue edges defining the aperture are welded and sealed to create a finished edge and thus prevent further tissue damage after the AV fistula is completed, and to hermetically seal the tissue to prevent blood loss.

The above noted energized member may comprise the toggle member, or a heater disposed in the toggle delivery catheter, or, preferably, both, so that the aperture creating step comprises energizing the toggle member and the heater, and applying the energized toggle member and the energized heater to opposing sides of the tissue through which the aperture is to be formed. The heater preferably comprises a heater insert which is removable from the toggle delivery catheter.

The invention, together with additional features and advantages thereof, may best be understood by reference to the following description taken in conjunction with the accompanying illustrative drawings.

BRIEF DESCRIPTION OF THE DRAWINGS

FIG. 13A is an isometric view of the sheath of FIG. 13;

FIG. 15 is a cross-sectional view of the catheter inserted into the vessel access sheath of FIG. 13, over a guidewire;

FIG. 16 is a cross-sectional view similar to FIG. 15 of the side access needle and guidewire inserted into the catheter;

FIG. 16A is an isometric view of the side access needle catheter shown in FIGS. 14-16;

FIG. 17 is a cross-sectional view of the toggle delivery catheter of the embodiment of FIGS. 13-16;

FIG. 18 is a cross-sectional view similar to FIG. 17, wherein the toggle delivery catheter has been inserted into the sheath;

FIG. 19 is a cross-sectional view similar to FIGS. 17 and 18 wherein the toggle member has been inserted over the side access guidewire;

FIG. 20 is an isometric view of the device as shown in FIG. 19;

FIG. 26 is a view similar to FIGS. 23-25, wherein the sheath has been advanced farther into the vessel;

FIG. 27 is a view similar to FIG. 26, wherein the side access needle catheter has been inserted through the sheath;

FIG. 28 is a view similar to FIG. 27, wherein the side access needle has been advanced into a second adjacent vessel;

FIG. 32 is a view similar to FIG. 31, wherein the toggle member has been advanced into the second vessel;

FIG. 33 is a view similar to FIG. 32 wherein the toggle member has rotated and adjusted its length to align with the plane of the vessel into which it was inserted, after which it has been withdrawn proximally to cinch the two vessels together;

FIG. 34 is a view similar to FIG. 33 wherein the toggle has been pulled through the walls of the two vessels;

FIG. 38 is an isometric view of the toggle insertion sheath of the toggle delivery catheter embodiment, illustrating multiple lumens for carrying power wires to the toggle heater insert;

FIG. 39 is an isometric view of one embodiment of a toggle heater insert;

FIG. 42 is an isometric view of a catheter tube for use with the catheter toggle delivery system, showing the end plug and power wires; and FIG. 43 is an isometric view of the catheter tube of FIG. 42, with the toggle heater insert in place.

DESCRIPTION OF THE PREFERRED EMBODIMENT

Figure 1:
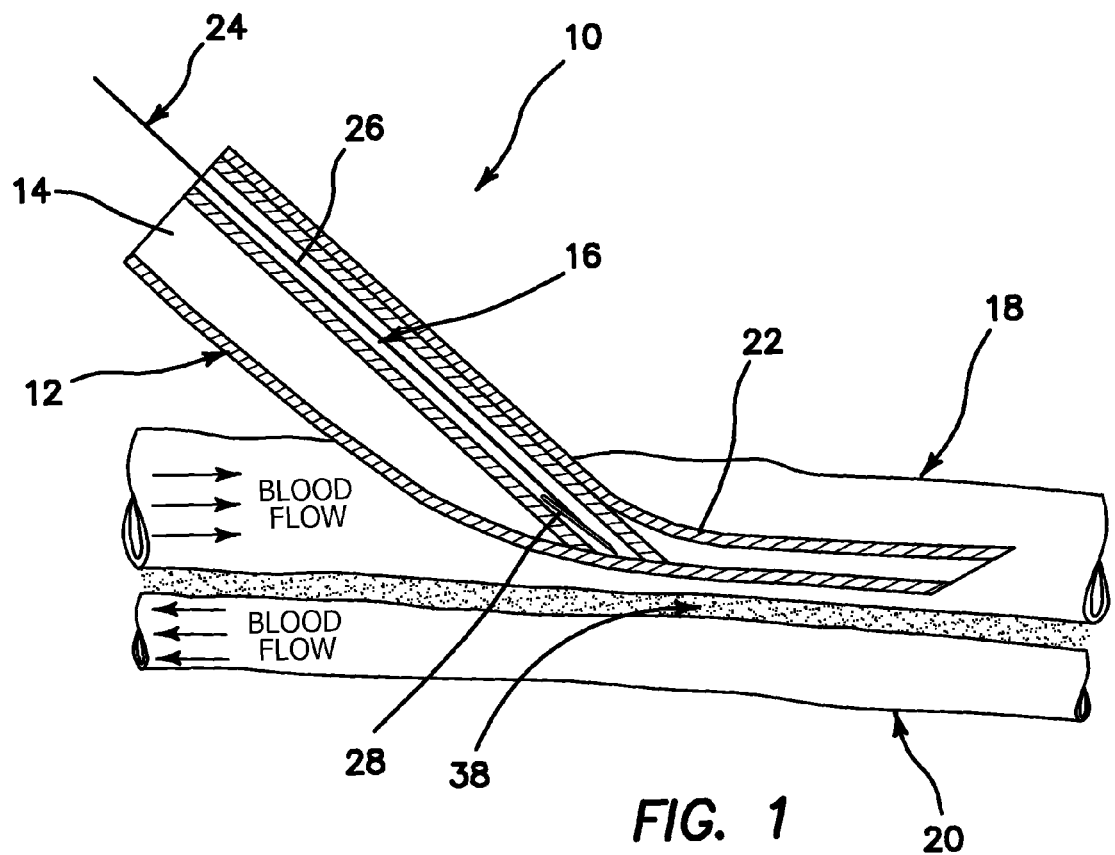
FIG. 1 is a view of one embodiment of the device of the present invention, wherein the device has been percutaneously or surgically positioned at a desired procedural location in a blood vessel.

Referring now more particularly to the drawings, there is shown in FIGS. 1-6 one embodiment of a device 10 constructed in accordance with the principles of the present invention. As illustrated in FIG. 1, the device 10 comprises a main body 12 having a primary lumen 14 and a secondary lumen 16. To begin the inventive method of creating an AV fistula, the practitioner selects an appropriate procedural site having each of a first blood vessel 18 and a second blood vessel 20 in close proximity to one another. In currently preferred approaches, the first blood vessel 18 comprises a vein, and the second blood vessel 20 comprises an artery, but the invention is not necessarily limited to this arrangement. The main body 12 is inserted into the first vessel 18, as illustrated, so that a distal end 22 thereof lies within the blood flow passage of the first vessel. Preferably, this insertion step is performed using a percutaneous technique, but surgery may also be employed, if desired.

Figure 2:
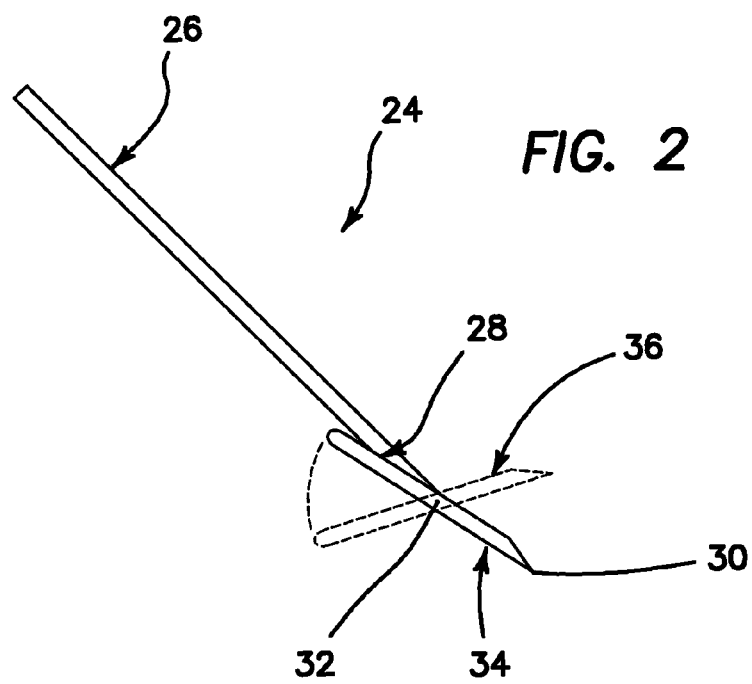
FIG. 2 is a view illustrating a shaft and toggle member of the present invention in isolation.

With reference now particularly to FIG. 2, a piercing toggle member 24, which comprises a part of the device 10, is shown. The piercing toggle member 24 comprises a shaft 26 and a toggle bar 28. The toggle bar 28 is preferably constructed to have a sharp point 30 on one end thereof. It is pivotally attached, by means of a hinge point 32, to a distal end of the shaft 26.

As illustrated in FIG. 2, the toggle bar 28 is pivotable between two primary orientations. A first, or closed, orientation 34 is shown in solid outline, while a second, or open, orientation 36 is shown in dotted outline. As will be described more fully below, the closed orientation 34 is utilized during the initial device insertion steps, as well as the device withdrawal steps, while the open orientation 36 is the operative orientation for creating the fistula. The toggle bar 28 is biased, by suitable means, to the closed orientation 34.

Referring once again to FIG. 1, it can be seen that the piercing toggle member 24 is inserted into the secondary lumen 16 of the main body 12, with the toggle bar 28 disposed, in its closed orientation 34, at a distal end of the secondary lumen.

Figure 3:
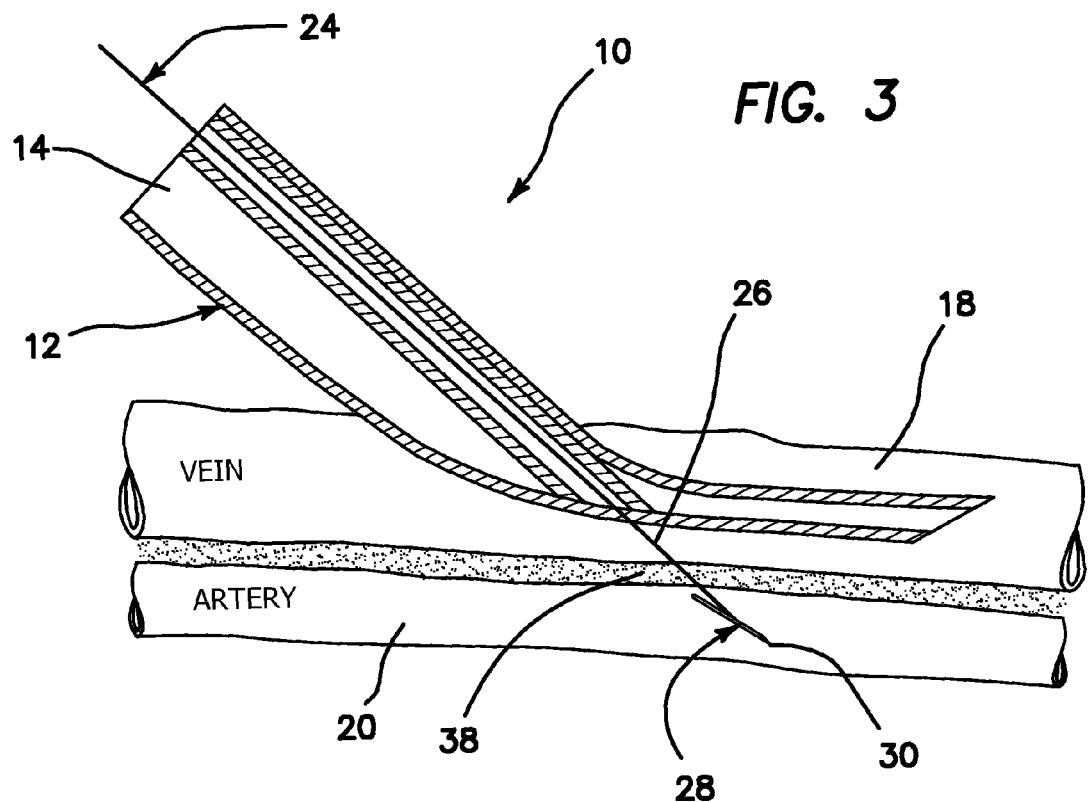
FIG. 3 is a view similar to FIG. 1, wherein the toggle member illustrated in FIG. 2 has been extended out of the first blood vessel and into an adjacent second blood vessel.

Now, with reference to FIG. 3, it can be seen that the piercing toggle member 24 has been advanced distally so that it has exited a distal end of the secondary lumen 16 and through an aperture (not shown) provided in the wall of the main body. Additionally, using the sharp point 30 of the toggle bar 28, in its closed orientation 34, the toggle bar 28 and shaft 26 has been advanced through the first vessel 18, piercing the wall of the first vessel, tissue 38 between the first vessel and the second vessel 20, and the wall of the second vessel 20, so that the toggle bar 28 and distal end of the shaft 26 is now disposed within the second vessel 20.

Figure 4:
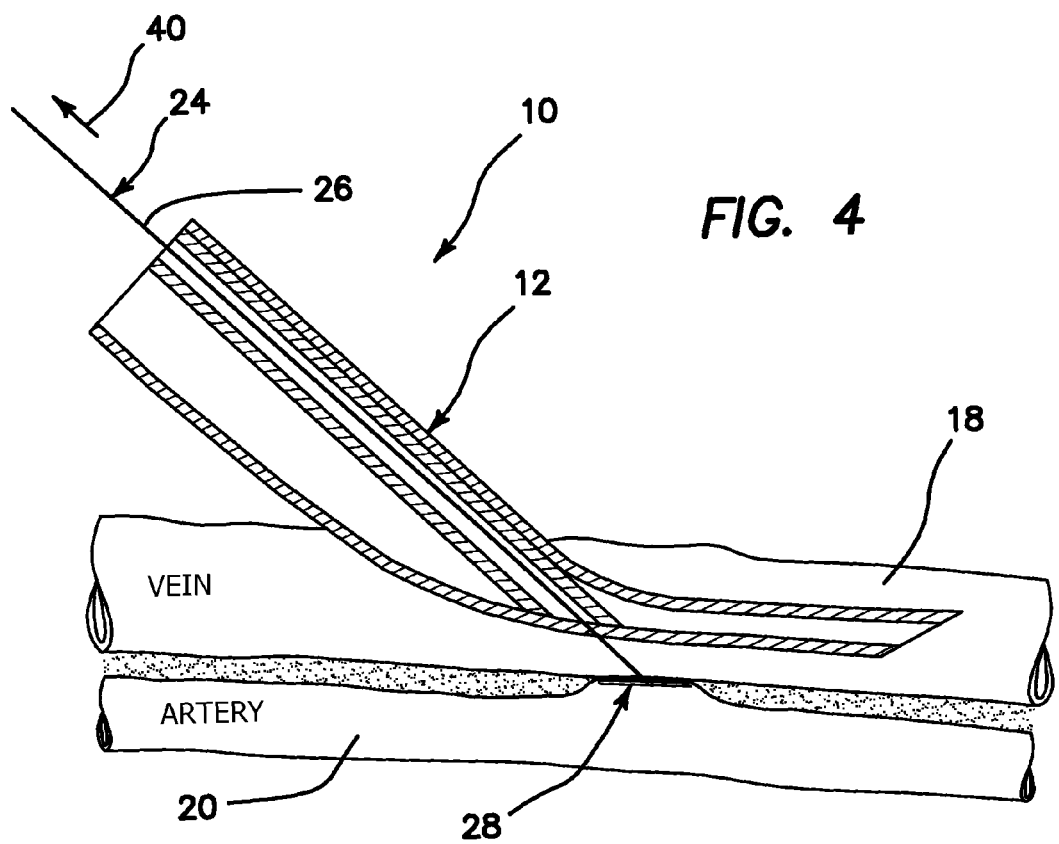
FIG. 4 is a view similar to FIG. 3, wherein tension has been applied to the toggle member to actuate it and to cause the second blood vessel to be pulled into a position closely adjacent to the first vessel.
Figure 5:
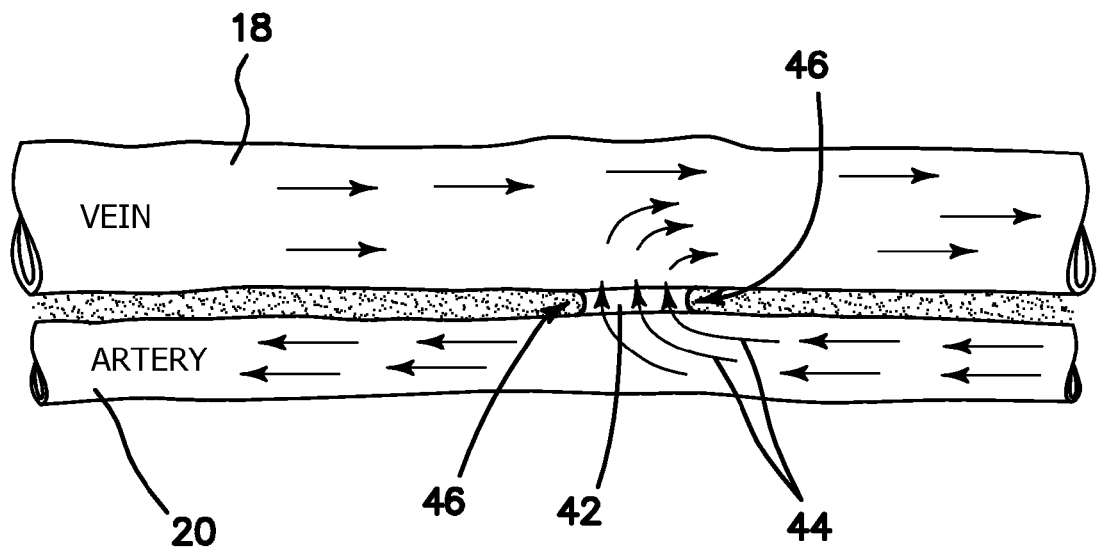
FIG. 5 illustrates the fistula created by the device and methods of the present invention after the inventive device of FIGS. 1-4 has been withdrawn from the procedural site.
Figure 6:
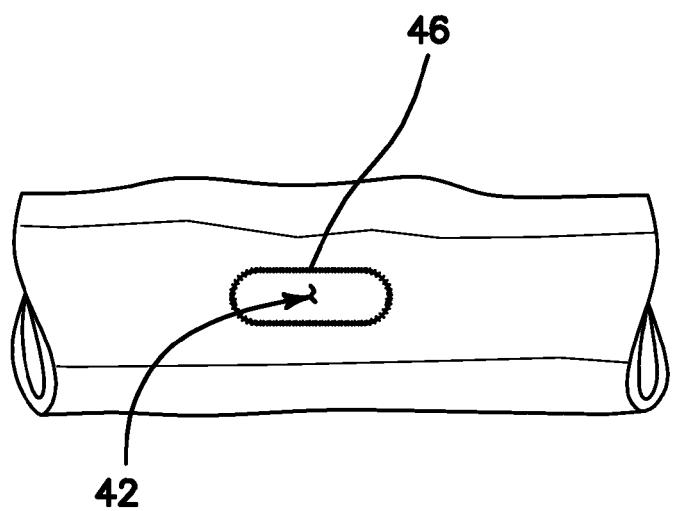
FIG. 6 illustrates a communicating lumen created between the first and second vessels.

Once the distal end of the piercing toggle member 24, and the toggle bar 28, is positioned within the second vessel 20, the toggle bar 28 may be pivoted or deployed to its open orientation 36, as shown in FIG. 4. Tensile force is then applied proximally on the shaft 26 of the piercing toggle member 24, along arrow 40, to move the toggle bar 28 into contact with the second vessel wall, at the selected location for the creation of an elongated aperture which will form the desired fistula. This action initially functions to pull the second vessel 20 into closer proximity to the first vessel 18. Then, in one embodiment, radio-frequency (RF) energy is applied to the toggle bar 28. The RF energy functions to burn an elongate aperture 42 through the opposing walls of each of the first vessel 18 and second vessel 20, as well as any intervening tissue 38. This elongate aperture 42 is shown in FIGS. 5 and 6. Alternative cutting approaches, such as resistive heat (hot wire), ultrasonic, laser, or mechanical approaches, may be used instead of RF energy, if desired.

As formed, the elongate aperture 42 will typically resemble a slit. However, as pressurized blood flow 44 begins to occur through the slit 42, which creates a communicating passage between the first vessel 18 and the second vessel 20, the slit widens responsive to the pressure to form the desired fistula. The edges 46 of the aperture are cauterized, following which the device 10 is removed from the procedural site.

Now, referring particularly to FIGS. 7-12, an alternative embodiment of a device 110 and methods of the present invention is described, wherein like reference numerals identify like elements, preceded by the numeral 1. This embodiment functions similarly to the embodiment of FIGS. 1-6 in many ways, but is significantly different as well. These differences will be emphasized in the following description.

Figure 7:
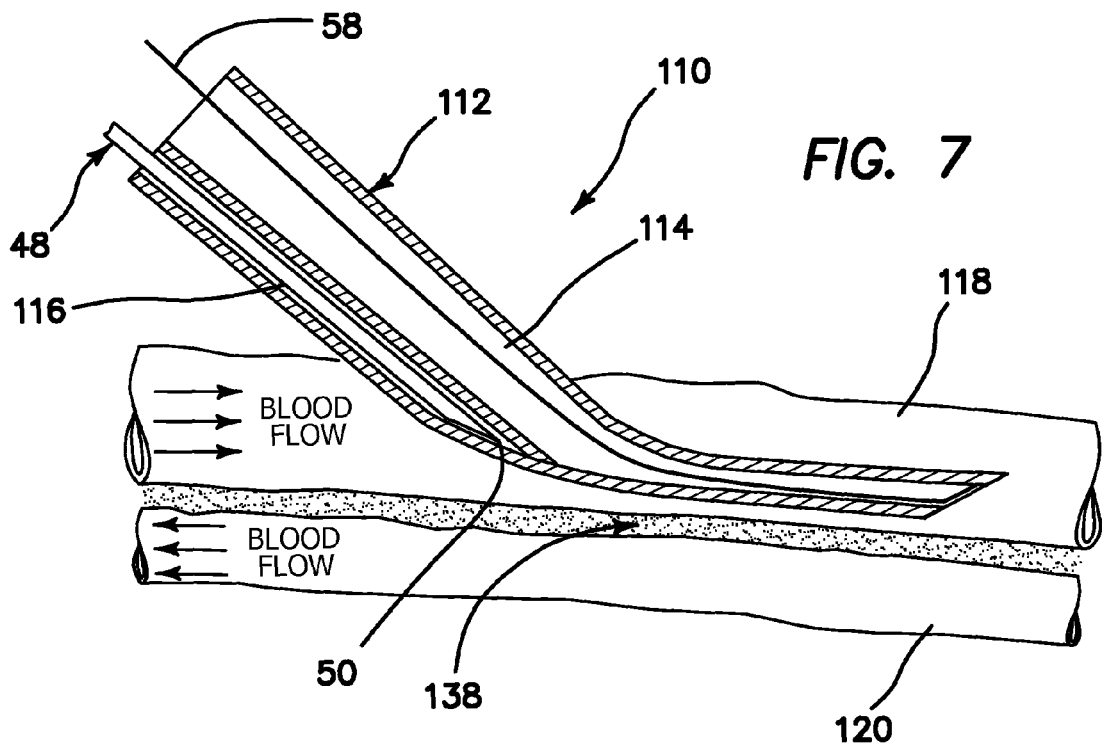
FIG. 7 is a view similar to FIG. 1 illustrating a second modified embodiment of the device of the present invention, wherein the device has been percutaneously or surgically positioned at a desired procedural location in a first blood vessel.

As in the previous embodiment, the device 110 comprises a main body 112 having a primary lumen 114 and a secondary lumen 116. As shown in FIG. 7, the device 110 is inserted, preferably percutaneously, into a first blood vessel 118 at a desired procedural site. A secondary piercing member 48 is inserted into the secondary lumen 116. This secondary piercing member 48 has a sharp distal end 50.

Figure 8:
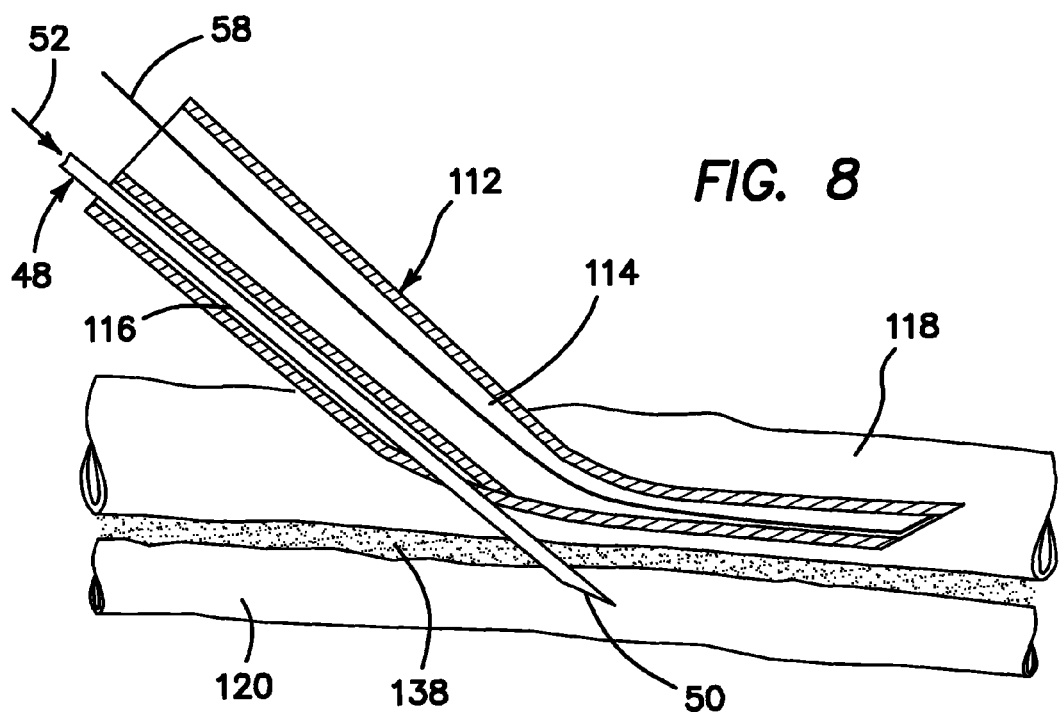
FIG. 8 is a view similar to FIG. 7, wherein the secondary piercing element of the device has been extended out of the first vessel and into an adjacent second vessel.

In FIG. 8, the secondary piercing member has been advanced distally, along the direction of arrow 52, so that the sharp distal end 50 exits the distal end of the secondary lumen 116 and an aperture (not shown) in the wall of the main body 112, extends through the first vessel 118 and its wall, tissue 138, and the wall of a second blood vessel 120. Thus, when fully extended, after piercing through the noted tissue, the sharp distal end 50 of the secondary piercing member 48 is disposed within the second vessel 120, as shown.

Figure 9:
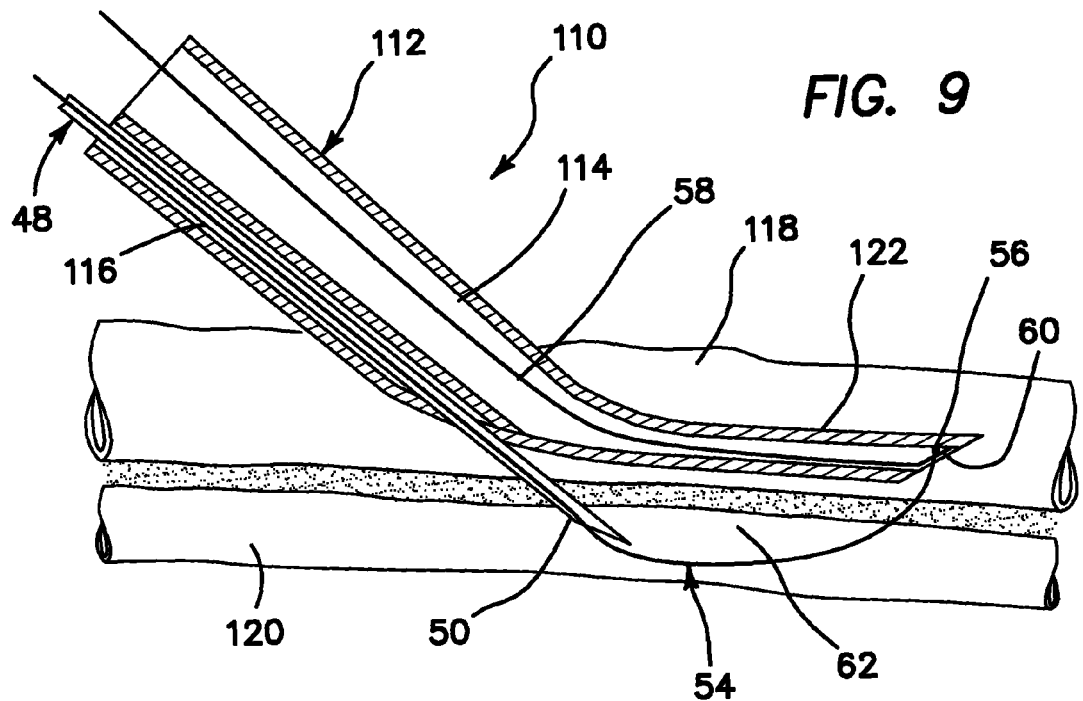
FIG. 9 is a view similar to FIGS. 7 and 8, wherein a preformed piercing needle has been extended from the secondary piercing element and into a distal end of the main body of the device.
Figure 10:
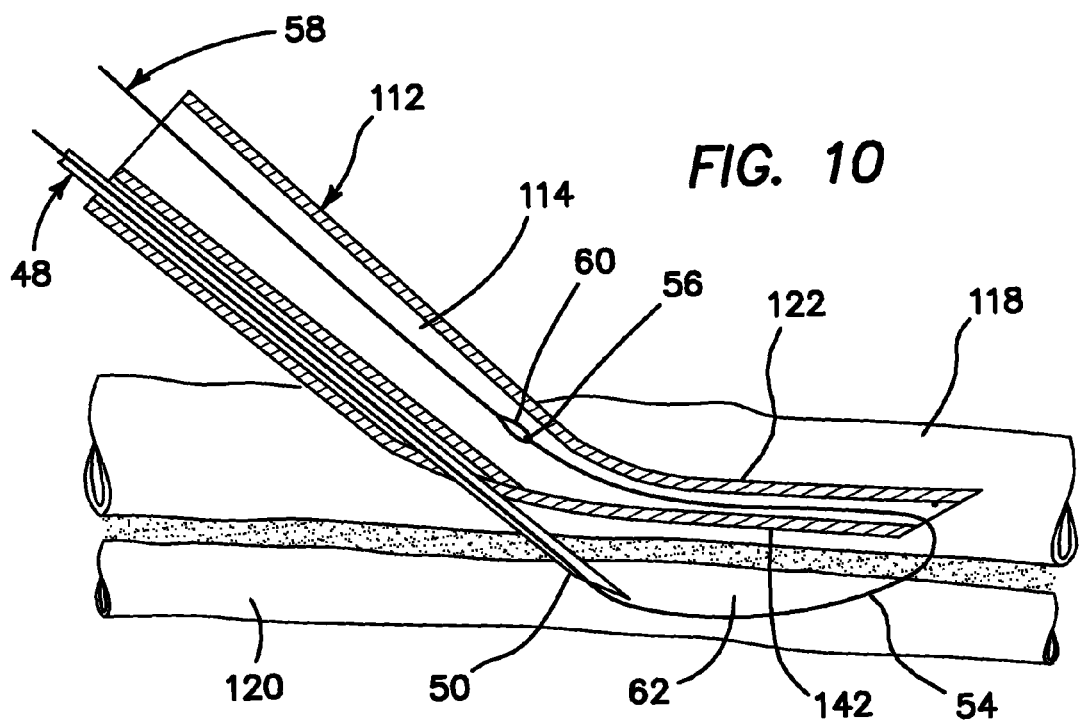
FIG. 10 is a view similar to FIG. 9, wherein a snare has been extended through the main body of the device to catch and secure, then proximally pull the piercing needle therethrough.
Figure 11:
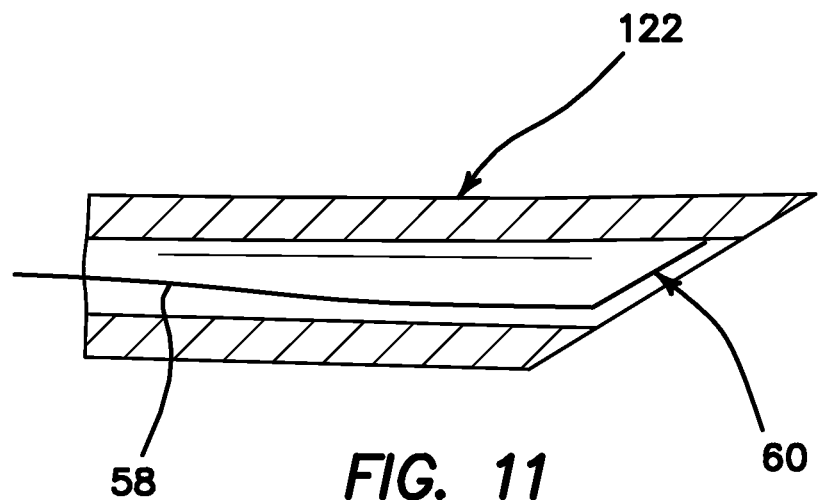
FIG. 11 is a side view of the distal tip of the main body in isolation.
Figure 12:
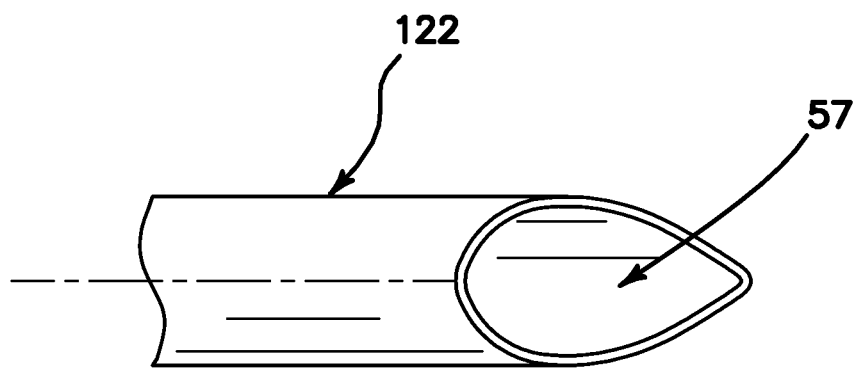
FIG. 12 is a top view of the distal tip shown in FIG. 11.
Figure 13:
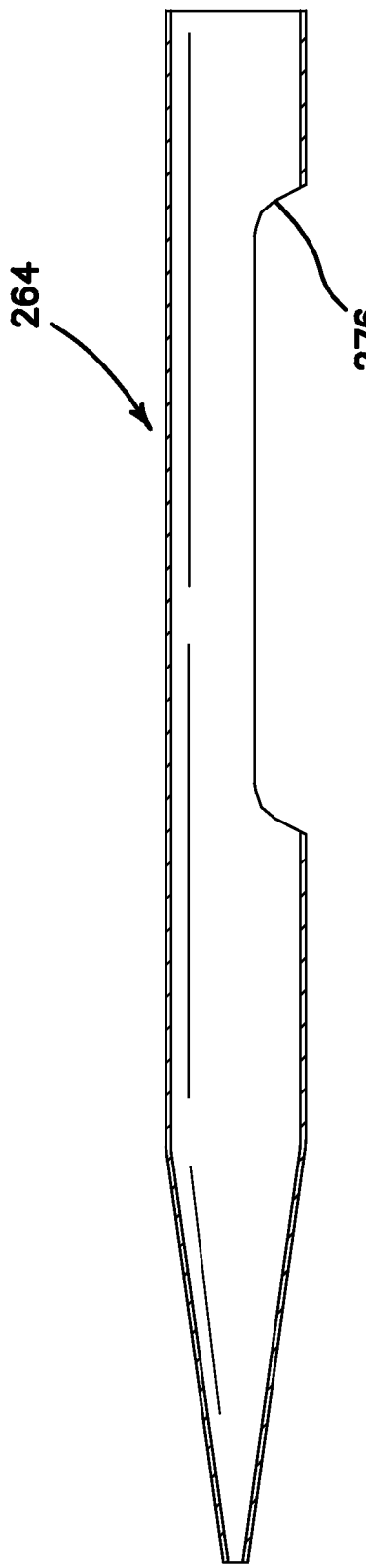
FIG. 13 is a plan view of a vessel access sheath for use in yet another embodiment of the present invention.

As shown now in FIG. 9, once the sharp distal end 50 of the secondary piercing member 48 is located within the second vessel 120, a preformed piercing needle 54, having a barb 56 on its distal end, is actuated to extend distally from the sharp distal end 50 of the secondary piercing member 48, back through the second vessel wall and into the distal end 122, and thus the primary lumen 114, of the main body 112 of the device 110. The distal end 122 of the main body 112 is illustrated in greater detail in FIGS. 11 and 12. The practitioner, in directing the needle 54, aims for a target area 57, as shown in FIG. 12. A pull wire 58, having a snare loop 60 on its distal end, is extended distally through the primary lumen 114, until the snare loop 60 engages and captures the barb 56. Then, as illustrated in FIG. 10, the pull wire 58 is retracted proximally, to firmly catch the piercing needle 54 with the barb 56, and to tighten the loop 62 formed by the piercing needle. Continuing to proximally withdraw the pull wire 58 will pull the wire loop 62 through the tissue forming the walls of both the first vessel 118 and the second vessel 120, as well as any intervening tissue 138, to form a desired elongated slit or aperture 142. If desired, the loop 62 may be energized to enhance the cutting action.

Figure 14A:
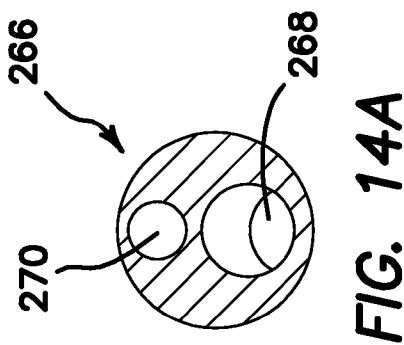
FIG. 14A is a cross-sectional view taken along the lines 14A-14A of FIG. 14.
Figure 14:
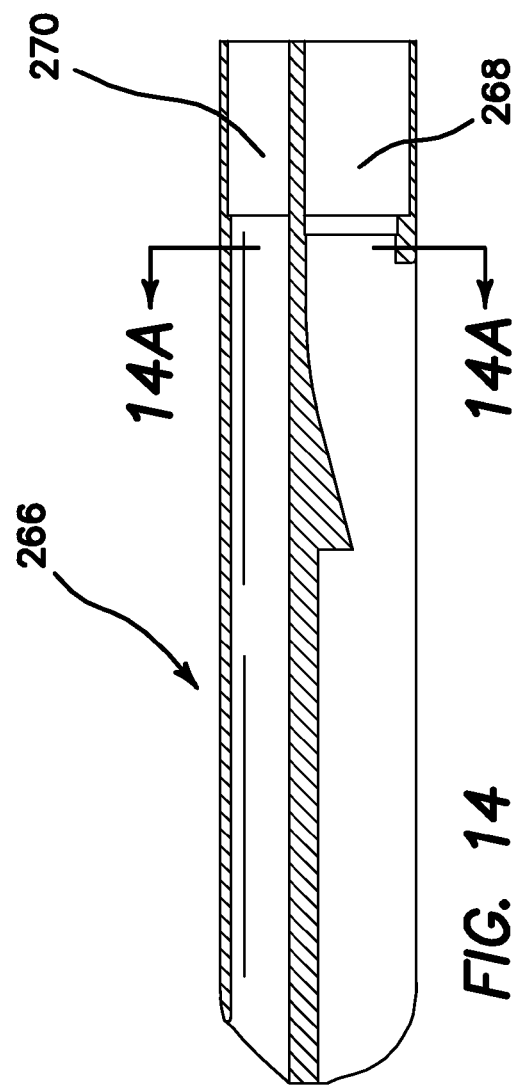
FIG. 14 is a cross-sectional view of the side access portion of a needle catheter for use with the sheath of FIG. 13.

There is shown in FIGS. 13-20 yet another embodiment of an AV fistula device or system 210 constructed in accordance with the principles of the present invention. The device 210 comprises a vessel access sheath 264 (FIGS. 13 and 13A) and a side access needle catheter 266 (FIGS. 14, 14A, 16A). The side access needle catheter 266 comprises a primary lumen 268 and a secondary lumen 270 (FIGS. 14 and 14A).

In FIG. 15, the side access needle catheter 266 has been inserted into the vessel access sheath 264, over a first guidewire 272. The first guidewire 272 extends through the secondary lumen 270, as shown.

FIGS. 16 and 16A further illustrate the system 210, particularly a side access needle catheter assembly of the system. As shown, a side access needle 274 has been inserted through a proximal end of the sheath 264 (the sheath is not shown in FIG. 16A, for clarity), extending distally through the primary lumen 268 and out of a side port 276 in the sheath 264. A second guidewire 278 is inserted through a proximal end of the side access needle 274, and out of a distal end thereof, as shown. The side access needle catheter assembly comprises each of the side access needle 274, side access catheter 266, and the second guidewire 278.

Now referring to FIGS. 17 and 18, a toggle delivery catheter 280 constructed in accordance with the principles of the present invention is shown. In FIG. 18, the toggle delivery catheter 280 has been inserted into the vessel access sheath 264 over the second guidewire 278. The toggle delivery catheter includes a side port 282, which is substantially coincident with the side port 276 of the vessel access sheath when the vessel access sheath 264 and toggle delivery catheter 280 are assembled as shown.

In FIGS. 19 and 20, a toggle apparatus 284, having a pivotable toggle member 285 attached to its distal end, has been inserted over the second guidewire 278 through the toggle delivery catheter 280, as shown.

The apparatus shown and described above in connection with FIGS. 13-20 will now be further described in conjunction with an explanation of a particular method by which the system 210 may be used to create an AV fistula. This method is illustrated more particularly in FIGS. 21-35.

Figure 21:
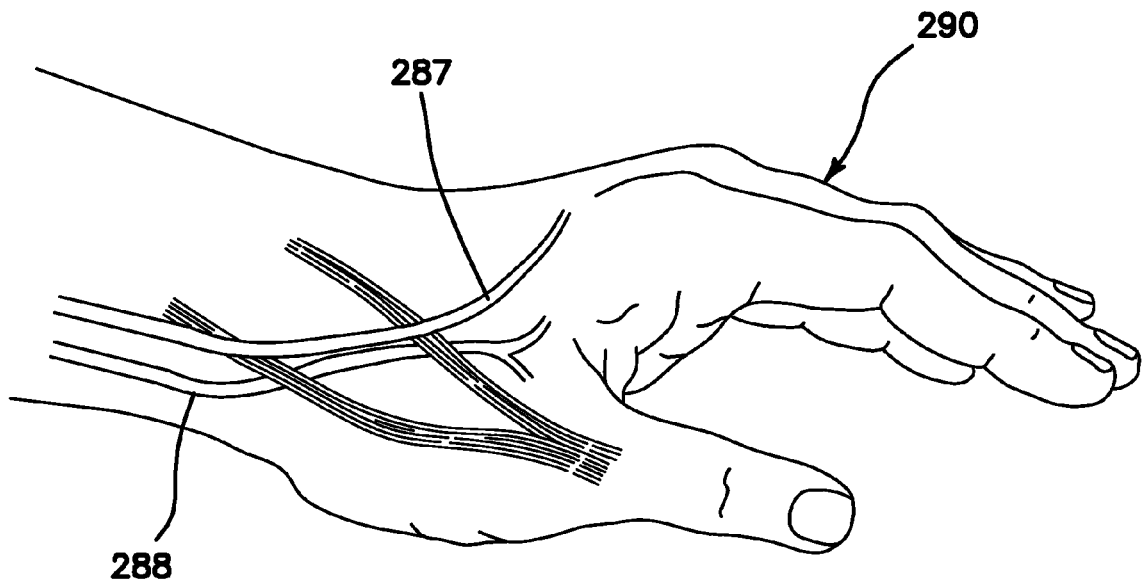
FIG. 21 is an isometric view showing the first step of an inventive method for creating an AV fistula in accordance with the principles of the present invention, using the toggle delivery catheter embodiment illustrated in FIGS. 13-20.
Figure 22:
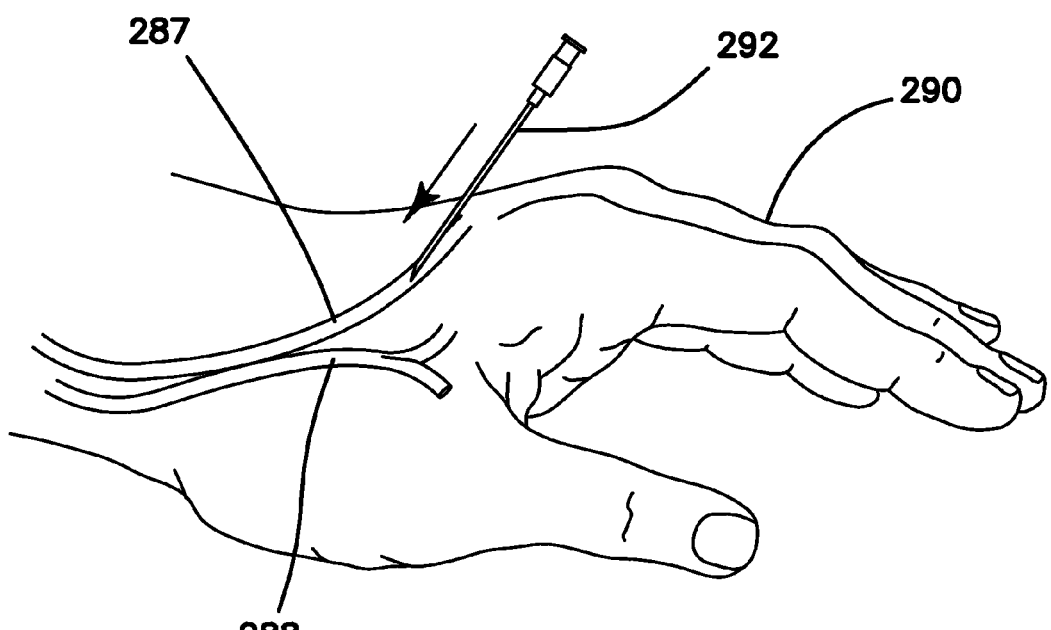
FIG. 22 is a view similar to FIG. 21, wherein a needle has been inserted into a vessel in the hand of a patient.
Figure 23:
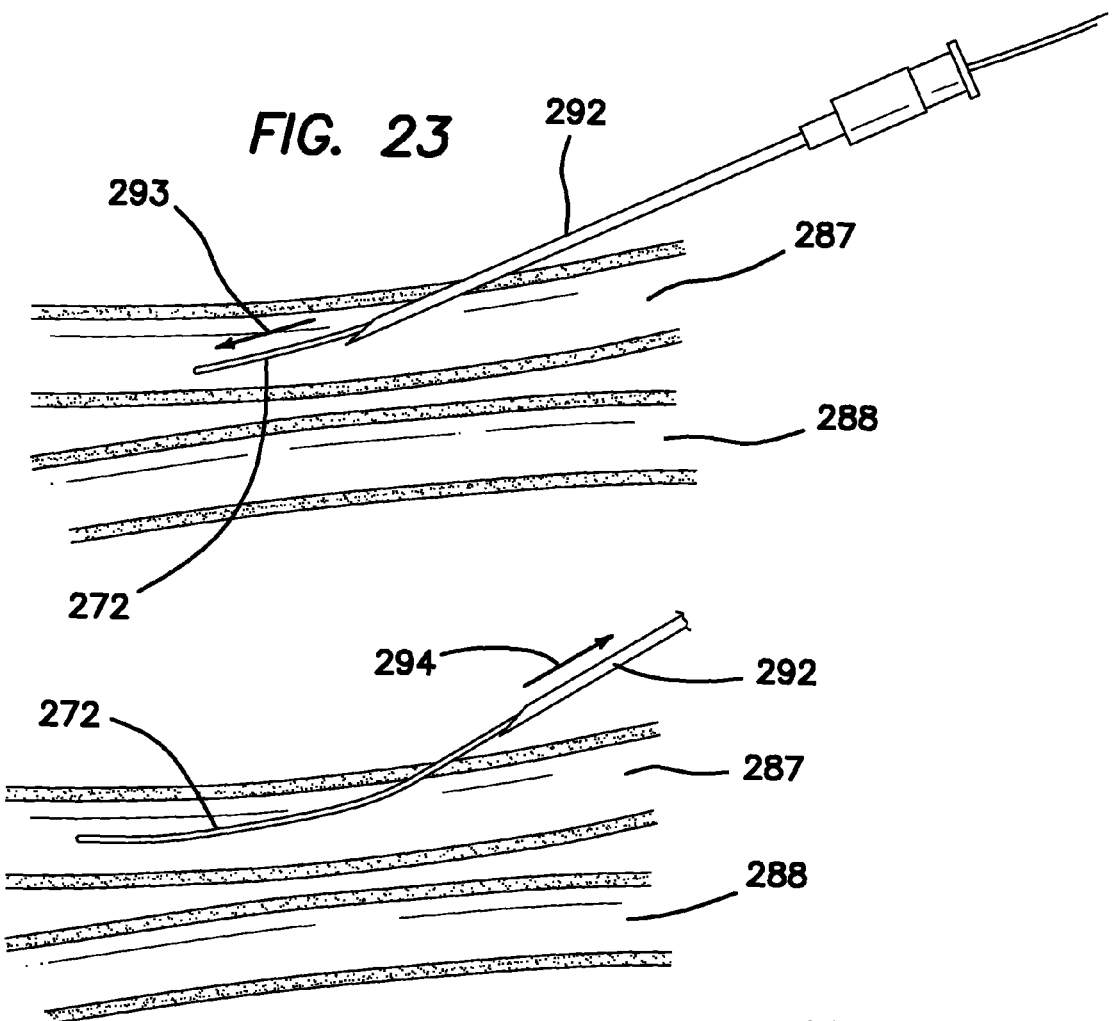
FIG. 23 is a view illustrating the insertion of a guidewire through the needle into the vessel.
Figure 24:
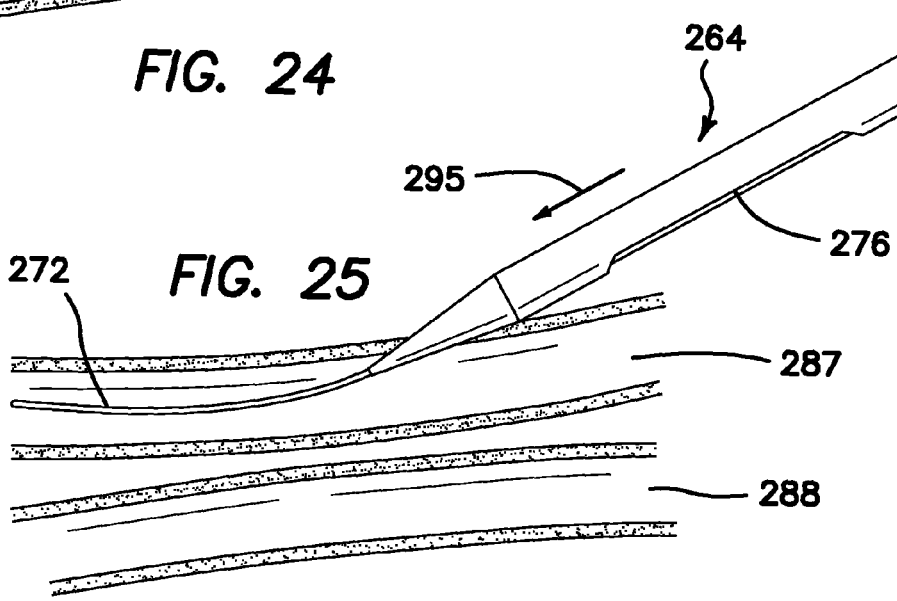
FIG. 24 is a view similar to FIG. 23 wherein the needle has been withdrawn and removed.

To begin the inventive method of creating an AV fistula, the practitioner selects an appropriate procedural site having each of a first vessel 287 and a second vessel 288 in close proximity to one another. In currently preferred approaches, the first vessel 287 comprises a vein, and the second vessel 288 comprises an artery, but the invention is not necessarily limited to this arrangement. As illustrated in FIG. 21, one presently preferred location is the hand 290 of a patient. Then, generally employing principles of the Seldinger technique, as shown in FIG. 22, the first vessel 287 is punctured by a needle 292, which is inserted therein. The first guidewire 272 is then inserted through the lumen of the hollow needle 292 into the vessel 287, and advanced in the direction of the arrow 293 (FIG. 23). Following this, as shown in FIG. 24, the needle 292 is removed, by withdrawing it in the direction of arrow 294.

Figure 25:
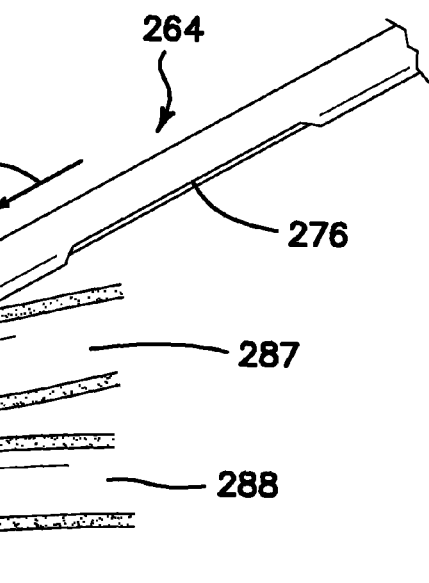
FIG. 25 is a view similar to FIGS. 23 and 24, wherein a sheath has been inserted over the guidewire.

The next step in the inventive method, as illustrated in FIG. 25, is to install the vessel access sheath 264 over the first guidewire 272 and into the first vessel 287, advancing the sheath 264 in the direction of arrow 295. Once the sheath 264 is fully inserted into the first vessel 287, so that the side port 276 is fully within the vessel, as shown in FIG. 26, the side access needle catheter 266 is installed into the sheath 264 in the direction of arrow 296 over the first guidewire 272, as illustrated in FIG. 27 (see also FIG. 15).

Figure 29:
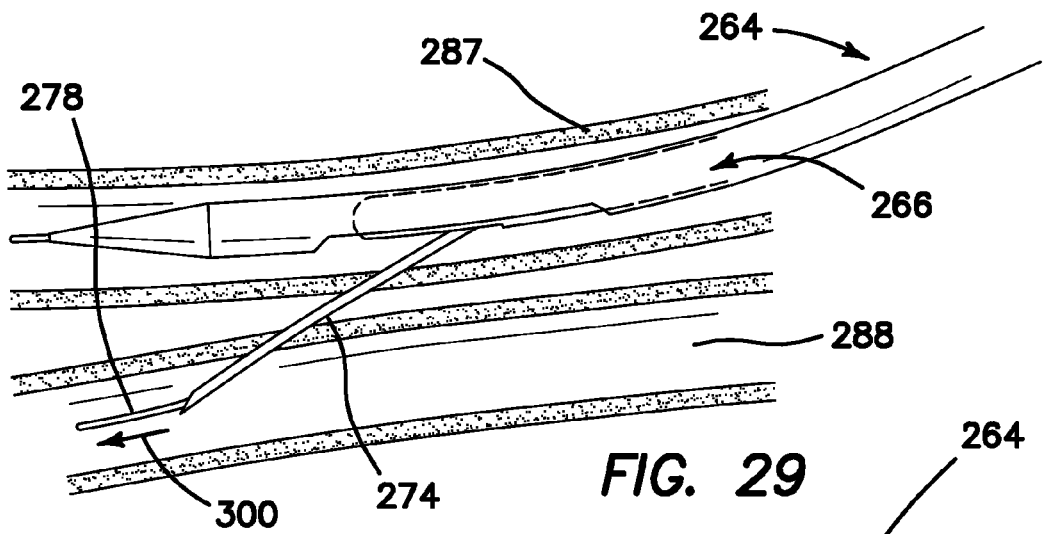
FIG. 29 is a view similar to FIG. 28, wherein a second guidewire has been advanced through the side access needle.

Now, referring particularly to FIGS. 28, 16, and 16A, the side access needle 274 is advanced out of the side access needle catheter 266 and through side port 276, in the direction of arrow 297. The side access needle 274 has a sharp distal tip 299, which punctures, respectively, the side walls of each of the first and second vessels 287, 288, as shown in FIG. 28, so that the distal end of the side access needle 274 is disposed in the interior of the second vessel 288. Then, as shown in FIGS. 29 and 16A, the second guidewire 278 is advanced through the lumen of the side access needle 274 and into the interior of the second vessel 288, in the direction of arrow 300.

Figure 30:
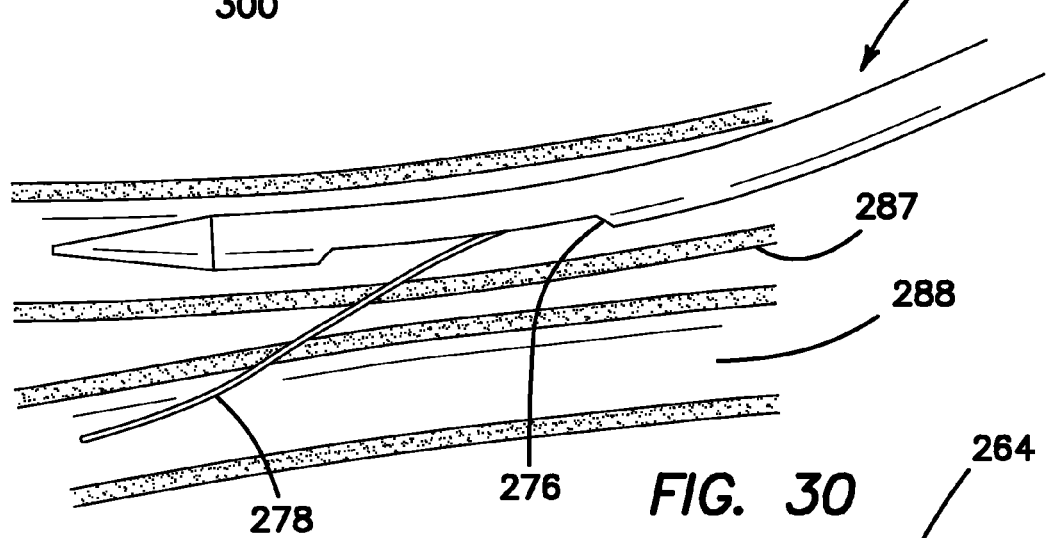
FIG. 30 is a view similar to FIG. 29, wherein the first guidewire, side access needle, and side access needle catheter have all been removed, and the second guidewire remains in position.

In FIG. 30, the first guidewire 272, side access needle 274, and side access needle catheter 266 have all been withdrawn from the procedural site, leaving the sheath 264 and second guidewire 278, which still extends from the first vessel 287 into the second vessel 288, as shown.

Figure 31:
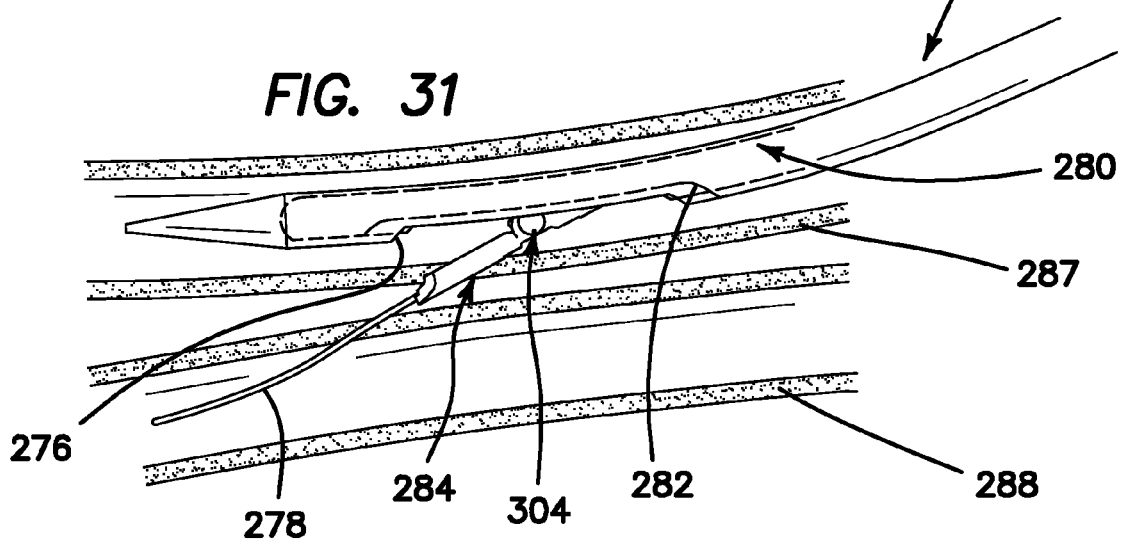
FIG. 31 is a view similar to FIG. 30, wherein the toggle delivery catheter with toggle member has been inserted, and the toggle member is being advanced over the second guidewire.

With reference now particularly to FIGS. 31, 17, and 18, the toggle delivery catheter 280 is inserted through the vessel access sheath 264 over the second guidewire 278. The toggle apparatus 284 is advanced out of the side port 276 of the sheath, as shown in FIG. 31, as well as in FIGS. 19 and 20. The toggle apparatus 284 comprises the toggle member 285, which is pivotably disposed on a toggle shaft 302 by means of a pivot joint 304.

In FIG. 32, the toggle apparatus 284 has been advanced over the second guidewire 278 (not shown in this figure) into the interior of the second vessel (artery) 288. To enter the vessel 288, the toggle member 285 is pivoted so that it is substantially parallel to the shaft 302, in a first, closed orientation, presenting essentially as the shaft 302 having a somewhat bulkier configuration at its distal end, and, optionally, a sharpened distal tip 305. Since the walls of both the first and second vessels have already been breached by the side access needle 274 earlier in the procedure, the toggle apparatus may be easily advanced into the second blood vessel 288, even without the assistance of the optional sharpened distal tip 305 or other cutting means. Once entry of the toggle member 285 into the second vessel 288 is achieved, the toggle member 285 is pivoted as illustrated in FIG. 32, to a second, open orientation, so that its lengthwise orientation is generally parallel to the direction of blood flow through the vessel.

Figure 35:
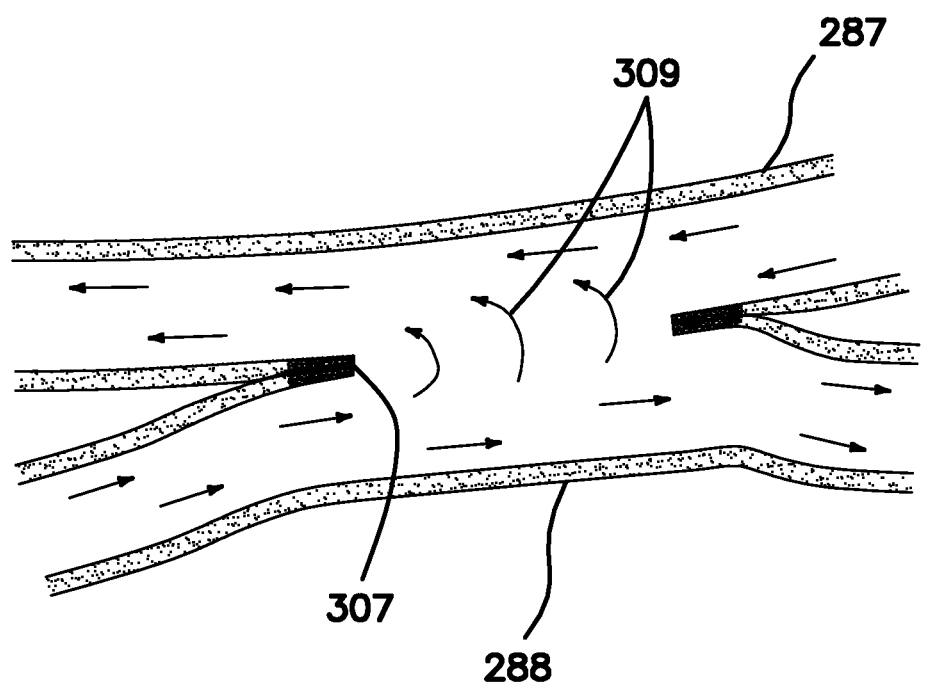
FIG. 35 illustrates a completed AV fistula after the toggle and access sheath have been removed.

At this point, as illustrated in FIG. 33, the toggle apparatus 284 is withdrawn proximally along the second guidewire 278, until the toggle member 285, in its open orientation, is pulled against the inner wall of the second vessel 288, at a location selected for the creation of an elongated aperture which will form the desired fistula. This action initially functions to pull the second vessel 288 into closer proximity to the first vessel 287. Then, in one embodiment, radio-frequency (RF) energy is applied to the length of the toggle member 285. The RF energy functions to burn and fuse or weld the vessels together, creating an elongate aperture 307 through the opposing walls of each of the first vessel 287 and second vessel 288, as well as any intervening tissue. This elongate aperture 307 is shown in FIGS. 34 and 35. Alternative cutting approaches, such as resistive heat (hot wire), ultrasonic, laser, or mechanical approaches, may be used instead of RF energy, if desired. Energy may also be applied to opposing surfaces of the toggle delivery catheter.

As formed, the elongate aperture 307 will typically resemble a slit, as shown in FIG. 34. However, as pressurized flow 309 begins to occur through the slit or aperture 307 (FIG. 35), which creates a communicating passage between the first vessel 287 and the second vessel 288, the aperture widens responsive to the pressure, taking the shape of an ellipse as it opens to form the desired fistula. The edges of the aperture are cauterized and welded, following which the device 210 is removed from the procedural site, as shown in FIG. 35. Tissue welding of the type intended to occur in the practice of these inventive methods is discussed in U.S. Pat. No. 6,908,463, to Treat et al., which is herein expressly incorporated by reference, in its entirety.

As noted above, particularly in connection with the discussion of FIGS. 33-35, an important feature of the present invention is the utilization of an energized apparatus, which may utilize RF energy, resistive heat, or other modalities as noted, to weld the tissue defining the aperture or communicating passage 307. This energy may be applied to the toggle, as noted above, or to a heater disposed in the catheter. In the present invention, however, Applicants have advantageously designed the system to apply energy to both the catheter and the toggle member. Thus, considering again FIGS. 19 and 20, a toggle heater 311 may be disposed on the underside of the toggle member 285. Additionally, a heater insert 313 is disposed within the catheter, on a side thereof, as shown in FIGS. 19 and 20. A key feature of this arrangement is that the catheter system has the ability to apply heat or RF energy to both toggle heater 311 on the toggle member 285 and to the heater insert 313 on the side of the catheter. In one resistive embodiment, the heater insert 313 is made of a resistive material that is connected to power wires, as will be described in more detail below. The surface of this heater insert 313 is designed to mate with the toggle member 285, so that when the toggle is pulled proximally against the heater insert 313, as shown in FIGS. 33-34, the system can be removed from the apparatus through the sheath, as noted above. However, this mating arrangement also allows pressure to be applied directly over the respective heating elements to induce cutting. The edges of the heater insert 313 can be designed to disperse heat through material changes or shape to promote a lower temperature specific to protein denaturization, around 120-175 F. This space on the side access toggle delivery catheter can also be filled with an ALNI (Aluminum Nitride Heater) or other high density heating elements, including versions of thick film and polyimide flex heaters. The heater insert 313 can also incorporate a collapsing motion or mechanism to facilitate removal, allowing the heater to move inwardly into the lumen space of the toggle delivery catheter. This motion of the heater insert 313 may also be employed to enhance cutting by allowing the toggle member 285 to move from the artery through the vein, and into the catheter. Finally, the direct mating and opposition of heater insert 313 to toggle surface is a primary mechanism, as described above, to apply direct pressure to the heating element.

Figure 36:
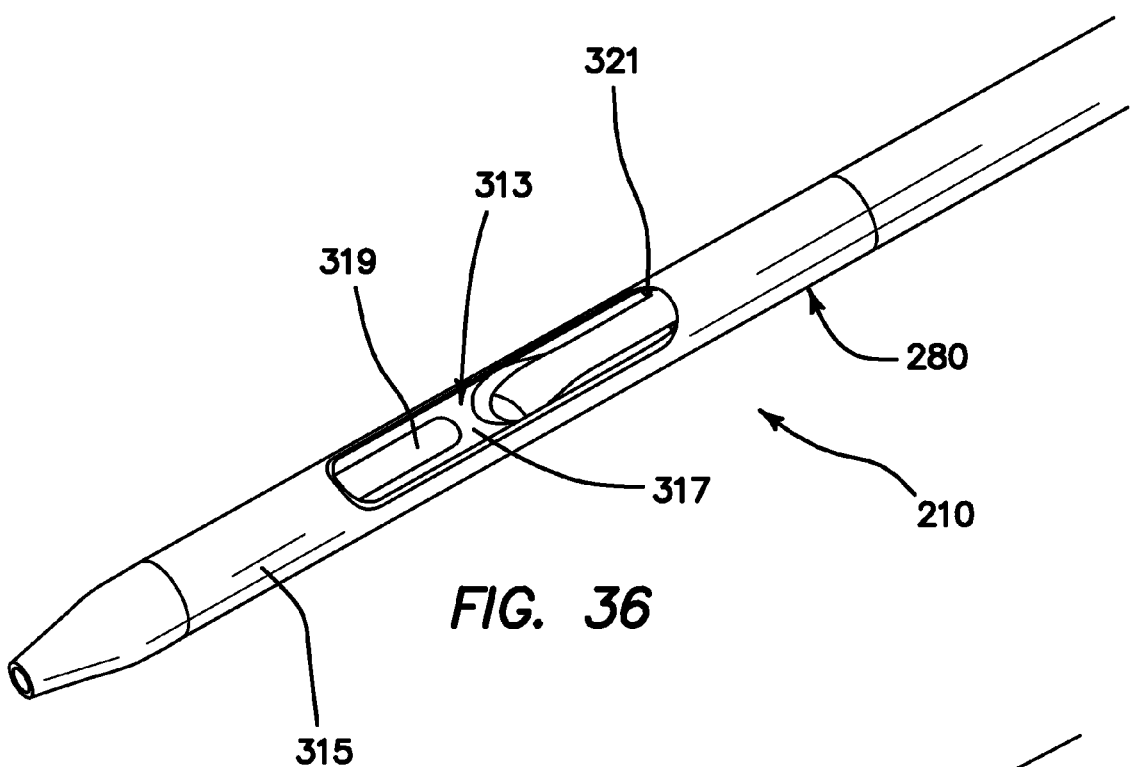
FIG. 36 is an isometric view of the toggle delivery catheter embodiment 210 of FIGS. 13-20, illustrating structural details of the toggle heater insert.
Figure 37:
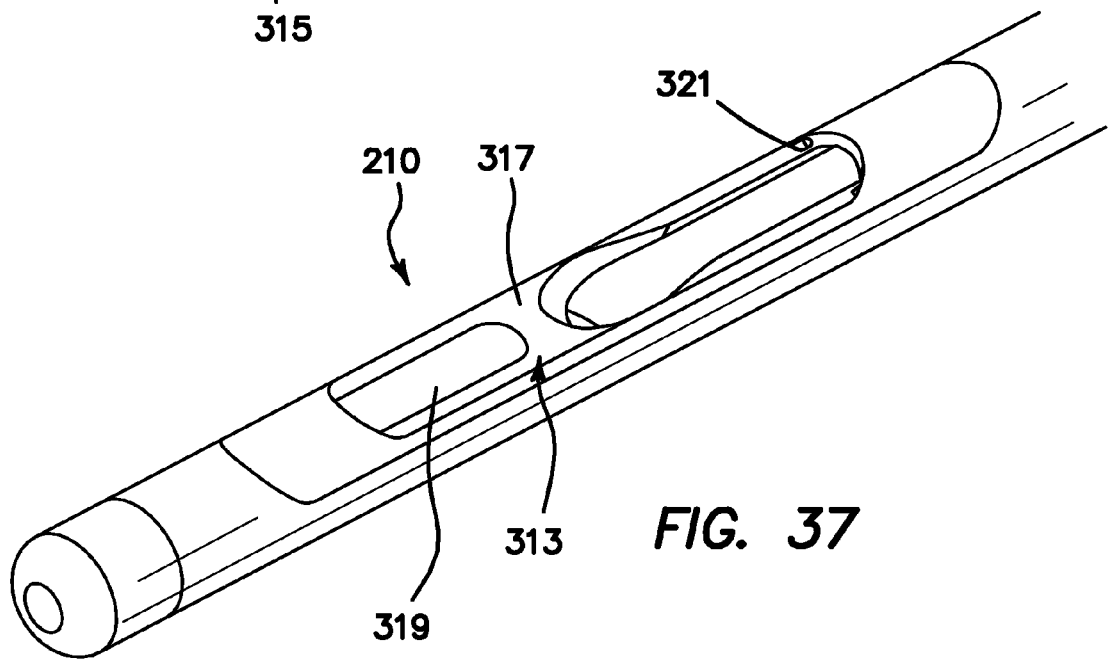
FIG. 37 is an isometric view similar to FIG. 36, wherein the heat shield has been removed for illustrative clarity.

Referring now to FIGS. 36-38, an embodiment of the catheter toggle delivery system 210 is shown which illustrates a little more clearly the particular features of the heating system, and especially of the heater insert 313. The toggle delivery catheter 280 comprises a heat shield 315. The heater insert 313 further comprises a weld cut zone 317 for mating with the toggle member 285, as discussed above. An end plug ramp insert 319 is also illustrated. The catheter tube 280 is machined to allow the heater insert 313 to sit down inside the shaft. Power wire inputs holes or lumens 321 (FIGS. 36 and 37) are formed in the heater insert 313 for receiving power connections for the heater. FIG. 38 illustrates the catheter tube 280, in isolation, and particularly shows that the catheter tube is machined with multiple lumens 323, which function to convey the power wires to the power wire inputs holes 321, for supplying energy to the heater system. It should be noted that, while two such lumens 323 are shown in FIG. 38, for illustrative purposes, the scope of the present invention contemplates differing numbers, depending upon design considerations for a particular application. For example, in one such alternative embodiment, four lumens 323 would be used.

Figure 40:
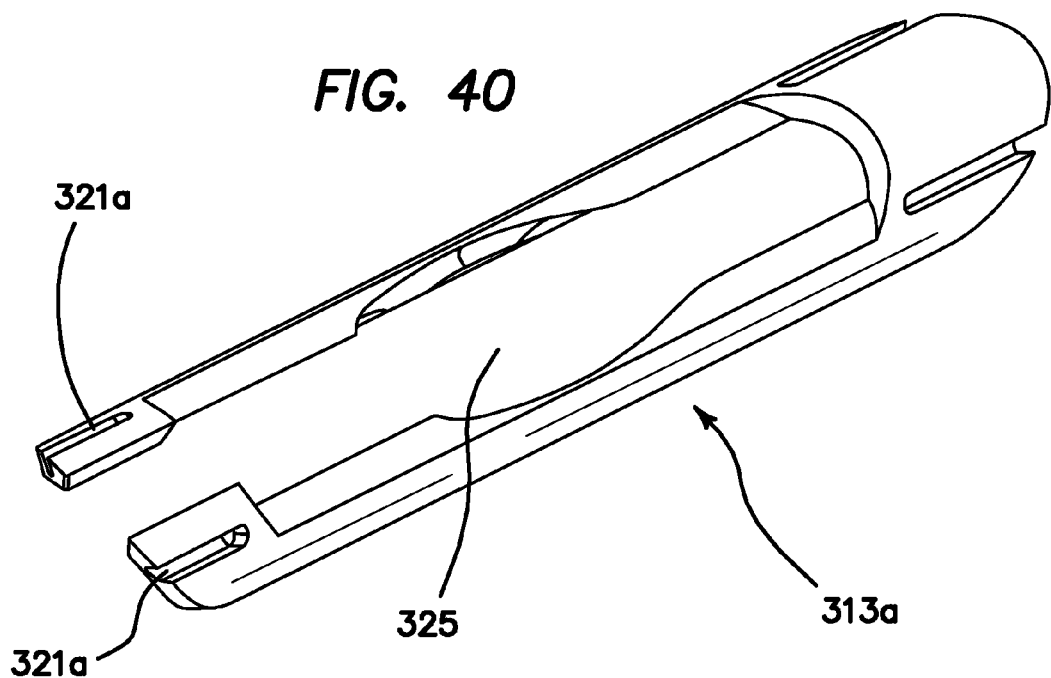
FIG. 40 is an isometric view of another embodiment of a toggle heater insert.

FIG. 39 illustrates one embodiment of the heater insert 313, apart from the system, as a whole, and thus more clearly showing its construction In FIG. 40, a modified embodiment of the heater insert 313a is shown. This embodiment particularly comprises power connection slots 321a, rather than holes, as well as a guide wire slot 325. The open distal end of this particular design functions to make manipulation of the heater insert easier.

Figure 41:
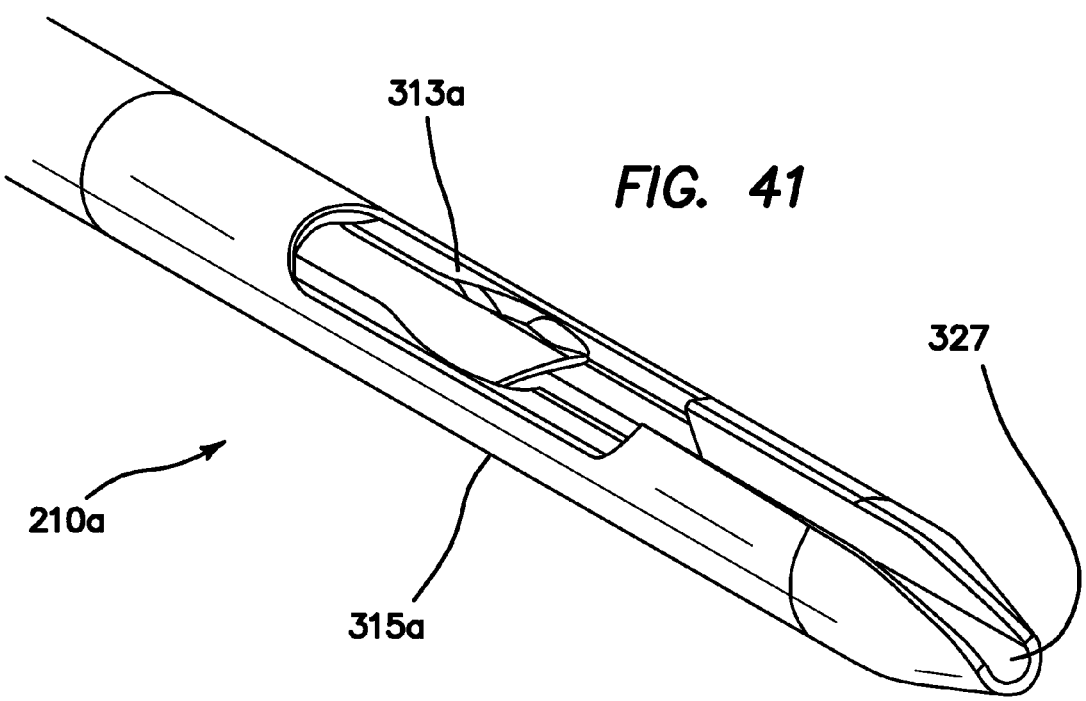
FIG. 41 is an isometric view of an embodiment of the catheter toggle delivery system, with toggle heater insert.

FIGS. 41-43 illustrate a somewhat modified embodiment 210a of the catheter toggle delivery system in accordance with the present invention. In this embodiment, like elements are identified by like reference numerals, succeeded by the letter a, and only the differing features are discussed. Specifically, this embodiment is designed to accommodate the modified heater insert 313a of FIG. 40, and includes a guide wire slot 327 in its distal end. An end plug 329 on the distal end of the catheter tube 280a is shown in FIGS. 42 and 43, which also includes a guide wire slot 331. Power wires 333, which run through the power wire lumens 323 and power wire inputs holes 321, for energizing the heater insert 313, 313a, are shown in FIG. 42.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. An apparatus, comprising:
a first portion having a proximal end and a distal end and an outer surface defining an opening;
a non-expandable second portion pivotably coupled to the first portion, the non-expandable second portion configured to be delivered through a lumen of the first portion and through a first body lumen and into a second body lumen;
a first energy delivery portion, separate from and fixedly coupled to, the first portion;
a second energy delivery portion, separate from and fixedly coupled to, the non-expandable second portion, the second energy delivery portion configured to directly mate with and oppose the first energy delivery portion; and
an actuator configured to move the non-expandable second portion from a first position disposed apart from a wall of the second body lumen to a second position adjacent to the wall of the second body lumen to apply pressure and energy sufficient to induce cutting and welding of body tissue between the first portion and the non-expandable second portion, the actuator having a shaft coupled to the non-expandable second portion, the shaft slidably positioned within the lumen of the first portion, the non-expandable second portion being opposed to the outer surface of the first portion such that a width of the non-expandable second portion when in the second position is greater than a greatest width of the opening of the first portion and the non-expandable second portion extends across the opening when in the second position.

2. The apparatus of claim 1, wherein the first portion and the non-expandable second portion are configured to be separated by a first distance when the apparatus is in a first configuration and the first portion and the non-expandable second portion are configured to be separated by a second distance when the apparatus is in a second configuration, the first distance being different than the second distance.

3. The apparatus of claim 1, wherein the first portion includes a distal end portion configured to engage a wall of the first body lumen at an angle orthogonal to an axis of the first portion.

4. The apparatus of claim 1, wherein the non-expandable second portion includes a surface configured to engage the wall of the second body lumen at an angle orthogonal to an axis of the non-expandable second portion.

5. The apparatus of claim 1, wherein the first portion includes a first surface and the non-expandable second portion includes a second surface, the first surface and the second surface being substantially parallel or coplanar.

6. The apparatus of claim 1, further comprising a feedback control device configured to control a temperature of at least one of the first energy delivery portion or the second energy delivery portion.

7. The apparatus of claim 1, wherein the non-expandable second portion is movable between a first configuration and a second configuration, the non-expandable second portion having a first lateral dimension in the first configuration and a second lateral dimension in the second configuration.

8. The apparatus of claim 1, wherein the actuator is configured to bias the non-expandable second portion in a single direction as the non-expandable second portion moves away from the first portion.

9. The apparatus of claim 1, wherein the first energy delivery portion is parallel to the second energy delivery portion when the second portion of the apparatus is in the second position.

10. The apparatus of claim 1, wherein the width of the second portion when in the second position and a width of the second energy delivery portion are greater than a smallest width of the opening of the first portion.

11. An apparatus, comprising:
a first portion having a proximal end and a distal end;
a shaft slidably coupled to the first portion;
a second portion pivotably coupled to the shaft at a center of the second portion and movably coupled to the first portion, the second portion configured to be delivered through a lumen of the first portion and through a first body lumen and into a second body lumen, the second portion being non-expandable;
a first portion of an energy delivery element fixedly coupled to the first portion of the apparatus;
a second portion of the energy delivery element operatively coupled to the second portion of the apparatus, the second portion of the energy delivery element including a raised portion extending from a surface of the second portion of the apparatus and disposed along a length of the surface of the second portion; and
an actuator configured to move the second portion of the apparatus from a first position disposed apart from a wall of the second body lumen to a second position adjacent the wall of the second body lumen, the raised portion of the second portion of the energy delivery element directly contacting and opposing the first portion of the energy delivery element when the second portion of the apparatus is in the second position.

12. The apparatus of claim 11, wherein the first portion of the energy delivery element and the second portion of the energy delivery element are configured to be actuated before the raised portion is adjacent the wall of the second body lumen.

13. The apparatus of claim 11, further comprising a feedback control device configured to control a temperature of the energy delivery element.

14. The apparatus of claim 11, wherein the first portion of the energy delivery element includes a surface configured to engage a body lumen wall at an angle orthogonal to an axis of the first portion of the apparatus.

15. The apparatus of claim 11, wherein the second portion of the energy delivery element includes a surface configured to engage a body lumen wall at an angle orthogonal to an axis of the second portion.

16. The apparatus of claim 11, wherein the first energy delivery portion is parallel to the second energy delivery portion when the second portion of the apparatus is in the second position.

17. A system, comprising:
a guidewire; and
an apparatus having
a first portion having a proximal end and a distal end and an outer surface defining a first opening;
a shaft slidably coupled to the first portion;
a non-expandable second portion pivotably coupled to the shaft at a center of the second portion and movably coupled to the first portion, the second portion configured to be delivered through a lumen of the first portion and through a first body lumen and into a second body lumen, the second portion defining a second opening;
a first energy delivery portion fixedly coupled to the first portion;
a second energy delivery portion fixedly coupled to the second portion; and
an actuator configured to move the second portion from a first configuration in which the second portion is disposed apart from the first portion at a first distance with no pressure or energy applied between the first portion and the second portion, and a second configuration in which the second portion is disposed apart from the first portion at a second distance, smaller than the first distance, with pressure and energy sufficient to induce cutting and welding of body tissue between the first portion and the second portion,
the actuator having a shaft coupled to the second portion, the shaft slidably positioned within the lumen of the first portion, the second portion being opposed to the outer surface of the first portion such that a width of the second portion when in the second position is not less than a width of the opening of the first portion, the second opening configured to contact the guidewire when the second portion is in the first configuration.

* * * * *